(12) United States Patent
Kuramoto

(10) Patent No.: US 9,913,568 B2
(45) Date of Patent: Mar. 13, 2018

(54) IMAGE PROCESSING DEVICE, METHOD FOR OPERATING THE SAME, AND ENDOSCOPE SYSTEM

(71) Applicant: FUJIFILM Corporation, Tokyo (JP)

(72) Inventor: Masayuki Kuramoto, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 15/215,771

(22) Filed: Jul. 21, 2016

(65) Prior Publication Data
US 2017/0032539 A1 Feb. 2, 2017

(30) Foreign Application Priority Data

Jul. 28, 2015 (JP) .................................. 2015-148250

(51) Int. Cl.
*A61B 1/00* (2006.01)
*A61B 1/04* (2006.01)
(Continued)

(52) U.S. Cl.
CPC .............. *A61B 1/0005* (2013.01); *A61B 1/04* (2013.01); *A61B 1/043* (2013.01); *A61B 1/0638* (2013.01); *A61B 1/0646* (2013.01); *A61B 1/0653* (2013.01); *G06T 7/0012* (2013.01); *G06T 7/90* (2017.01); *H04N 1/6005* (2013.01); *H04N 1/6008* (2013.01); *H04N 5/2256* (2013.01); *H04N 5/23293* (2013.01); *G06T 2207/10024* (2013.01); *G06T 2207/10068* (2013.01); *G06T 2207/10152* (2013.01);
(Continued)

(58) Field of Classification Search
USPC ......................................................... 382/128
See application file for complete search history.

(56) References Cited

U.S. PATENT DOCUMENTS

| 4,926,247 | A | * | 5/1990 | Nagasaki | ................. | H04N 9/68 |
| | | | | | | 257/232 |
| 5,649,021 | A | * | 7/1997 | Matey | ...................... | G06K 9/46 |
| | | | | | | 348/65 |

(Continued)

FOREIGN PATENT DOCUMENTS

| EP | 2803313 A1 | 11/2014 |
| JP | 5647752 B1 | 1/2015 |
| WO | WO 2014-156938 A1 | 10/2014 |

OTHER PUBLICATIONS

Extended European Search Report for European Application No. 16179473.0, dated Dec. 5, 2016.

*Primary Examiner* — Ishrat I Sherali
(74) *Attorney, Agent, or Firm* — Birch, Stewart, Kolasch & Birch, LLP

(57) ABSTRACT

First RGB image signals are subjected to an input process. First color information is obtained from the first RGB image signals. Second color information is obtained by a selective expansion processing in which color ranges except a first color range are moved in a feature space formed by the first color information, the first color information that represents each object in a body cavity being distributed in the each color range. The second color information is converted to second RGB signals. A red display signal, a green display signal and a blue display signal are obtained by applying a pseudo-color display process to the second RGB signals.

14 Claims, 25 Drawing Sheets

(51) Int. Cl.
  *A61B 1/06*   (2006.01)
  *H04N 1/60*   (2006.01)
  *H04N 5/225*  (2006.01)
  *H04N 5/232*  (2006.01)
  *G06T 7/90*   (2017.01)
  *G06T 7/00*   (2017.01)

(52) U.S. Cl.
  CPC ............ *G06T 2207/30092* (2013.01); *G06T 2207/30096* (2013.01); *H04N 2005/2255* (2013.01)

(56) References Cited

U.S. PATENT DOCUMENTS

| | | | | |
|---|---|---|---|---|
| 6,080,104 | A * | 6/2000 | Ozawa | H04N 5/2351 348/69 |
| 6,456,317 | B1 * | 9/2002 | Matsumoto | H04N 5/2352 348/68 |
| 8,253,783 | B2 * | 8/2012 | Takayama | A61B 1/042 348/222.1 |
| 9,582,878 | B2 * | 2/2017 | Kuramoto | G02B 23/24 |
| 9,754,189 | B2 * | 9/2017 | Mitsui | G06K 9/6257 |
| 2015/0080653 | A1 | 3/2015 | Terakawa | |
| 2015/0109350 | A1 | 4/2015 | Gotoh et al. | |
| 2016/0007829 | A1 | 1/2016 | Chun | |
| 2016/0171718 | A1 * | 6/2016 | Kuramoto | G06T 7/408 382/128 |

* cited by examiner

IMAGE PROCESSING DEVICE, METHOD FOR OPERATING THE SAME, AND ENDOSCOPE SYSTEM

CROSS-REFERENCE TO RELATED APPLICATIONS

The present application claims priority under 35 U.S.C. § 119 to Japanese Patent Application No. 2015-148250, filed Jul. 28, 2015. Each of the above application(s) is hereby expressly incorporated by reference, in its entirety, into the present application.

BACKGROUND OF THE INVENTION

1. Field of the Invention

The present invention relates to an image processing device, an endoscope system and a method for operating an image processing device, that generate an image obtained by imaging an object in a subject body.

2. Description Related to the Prior Art

In medical fields, diagnoses utilizing endoscope systems have been widely performed. The endoscope system comprises a light source device, an endoscope, and a processor device. In the endoscope system, illumination light is applied from an endoscope to a region of interest (object), and an image of the object is displayed on a monitor based on an image signal obtained by imaging the object illuminated with the illumination light. A doctor detects the presence or absence of a lesion while observing the image displayed on the monitor.

It is known that gastric (stomach) cancer causes atrophy of gastric mucosa, which makes the color of the gastric mucosa to fade. For this reason, there is a difference in color between the atrophic mucosa and the normal mucosa. The stomach cancer is diagnosed by observing the difference in color between the suspected lesion and the normal portion with an endoscope. "ABC method (ABC screening)" is recommended by the authorized nonprofit organization "Japan Research Foundation of Prediction, Diagnosis and Therapy for Gastric Cancer".

In advanced stages of atrophy (for example, groups C or D in the ABC screening), the difference in color between the normal portion and the atrophic portion is clear, so that it is easy to detect the atrophic portion. However, in intermediate stages (for example, groups B and C in the ABC screening), there is little difference in color between the atrophic portion and the normal portion. Therefore it is difficult to detect the atrophic portion based only on the difference in color.

In consideration of the above problem, United States Patent Application Publication No. 2016/0007829 (corresponding to Japanese Patent Publication No. 5647752) performs a color difference enhancing process which increases a difference between first and second signal ratios in a first color range and first and second signal ratios in a second color range to enhance a color difference between an atrophic portion and a normal portion, in a space formed by the first signal ratio between image signals of two colors out of three color image signals and a second signal ratio between image signals of two colors different from the first signal ratio.

However, the diagnosis of the lesion should be made in consideration of vascular states such as vascular patterns, in addition to the color difference between the normal portion and the lesion. Accordingly, in addition to enhance the color difference between the normal portion and the lesion as in United States Patent Application Publication No. 2016/0007829, it is required to emphasize blood vessels in an object and improve vascular visibility.

SUMMARY OF THE INVENTION

An object of the present invention is to provide an image processing device, an endoscope system and a method for operating an image processing device, that emphasizes a color difference between a normal part and an abnormal part in an object and improves vascular visibility of the object.

An aspect of the present invention provides an image processing device comprising an input processor, a color information obtaining processor, an expansion processor, and an RGB signal converter and a pseudo-color display processor. The input processor performs an input process of a first red signal, a first green signal and a first blue signal. The color information obtaining processor obtains first color information from the first red signal, the first green signal and the first blue signal. The expansion processor obtains second color information by a selective expansion processing in which color ranges except a first color range are moved in a feature space formed by the first color information. The first color information that represents each object in a body cavity is distributed in the each color range. The RGB signal converter converts the second color information to a second red signal, a second green signal and a second blue signal. The pseudo-color display processor obtains a red display signal, a green display signal and a blue display signal by applying a pseudo-color display process to the second red signal, the second green signal and the second blue signal.

It is preferable that the pseudo-color display process is a first color tone converting process to convert the second blue signal to the blue display signal and the green display signal and convert the second green signal to the red display signal. It is preferable that the pseudo-color display process is a second color tone converting process to obtain the blue display signal by applying a first weighting operation to the second blue signal and the second red signal, obtain the green display signal by applying a second weighting operation to the second blue signal and the second red signal, and obtain the red display signal by applying a third weighting operation to the second green signal and the second red signal.

It is preferable that the expansion processor includes an angle adjuster to perform an equal angular magnification process and an angle adjustment process in the feature space as the selective expansion processing. An angle in a region R1$x$ including a first reference line passing through the first color range is maintained unchanged based on an angle change rate W1$x$ in the equal angular magnification process. An angle in a region R1$y$ located outside the region R1$x$ is changed based on an angle change rate W1$y$ greater than or less than the angle change rate W1$x$ in the angle adjustment process.

It is preferable that the expansion processor includes a radial-coordinate adjuster to perform an equal radial-coordinate magnification process and a radial-coordinate adjustment process in the feature space as the selective expansion processing. A radial coordinate in a region R2$x$ including a second reference line passing through the first color range and intersecting the first reference line passing through the first color range is maintained unchanged based on a radial-coordinate change rate W2$x$ in the equal radial-coordinate magnification process. A radial coordinate in a region R2$y$ located outside the region R2$x$ is changed based on a radial-coordinate change rate W2y greater than or less than the radial-coordinate change rate W2x in the radial-coordinate adjustment process.

It is preferable that the first color information is a first signal ratio between the image signals of the two colors out of the first red signal, the first green signal and the first blue signal and a second signal ratio between the image signals of the two colors different from the first signal ratio, and the feature space is formed by the first signal ratio and the second signal ratio. It is preferable that the first color information is chrominance signals Cr and Cb, and the feature space is formed by the chrominance signals Cr and Cb. It is preferable that the first color information is components a* and b* of color information of CIE Lab space, and the feature space is formed by the color components a* and b*. It is preferable that the first color information is hue and saturation, and the feature space is formed by the hue and the saturation.

It is preferable that the image processing device further comprises a brightness adjuster to adjust a pixel value of the second red signal, the second green signal and the second blue signal based on first brightness information obtained from the first red signal, the first green signal and the first blue signal and second brightness information obtained from the second red signal, the second green signal and the second blue signal.

An aspect of the present invention provides an endoscope system comprising an image sensor, an input processor, a color information obtaining processor, an expansion processor, and an RGB signal converter and a pseudo-color display processor. The image sensor images an object in a body cavity. The input processor performs an input process of a first red signal, a first green signal and a first blue signal output from the image sensor. The color information obtaining processor obtains first color information from the first red signal, the first green signal and the first blue signal. The expansion processor obtains second color information by a selective expansion processing in which color ranges except a first color range are moved in a feature space formed by the first color information. The first color information that represents each object in a body cavity is distributed in the each color range. The RGB signal converter converts the second color information to a second red signal, a second green signal and a second blue signal. The pseudo-color display processor obtains a red display signal, a green display signal and a blue display signal by applying a pseudo-color display process to the second red signal, the second green signal and the second blue signal.

It is preferable that the endoscope system further comprises a light source to irradiate at least one of violet light and blue light in addition to green light and red light to the above object, and a source controller to independently control a light quantity of at least the one of violet light and blue light, a light quantity of the green light and a light quantity of the red light. The source controller performs a specific light quantity control to make the light quantity of at least the one of violet light and blue light and the light quantity of the green light larger than the light quantity of the red light. It is preferable that the image sensor has a blue pixel, a green pixel and a red pixel, and the endoscope system further comprises an image controller to control the blue pixel, the green pixel and the red pixel. The image controller performs a specific imaging control to make the sensitivities of the blue pixel and the green pixel higher than the sensitivity of the red pixel.

An aspect of the present invention provides a method for operating an image processing device comprising an image signal inputting step, a color information obtaining step, an expansion step, an RGB signal converting step and a pseudo-color displaying step. In the image signal inputting step, an input processor performs an input process of a first red signal, a first green signal and a first blue signal. In the color information obtaining step, a color information obtaining processor obtains first color information from the first red signal, the first green signal and the first blue signal. In the expansion step, an expansion processor obtains second color information by a selective expansion processing in which color ranges except a first color range are moved in a feature space formed by the first color information. The first color information that represents each object in a body cavity is distributed in the each color range. In the RGB signal converting step, an RGB signal converter convers the second color information to a second red signal, a second green signal and a second blue signal. In the pseudo-color displaying step, a pseudo-color display processor obtains a red display signal, a green display signal and a blue display signal by applying a pseudo-color display process to the second red signal, the second green signal and the second blue signal.

According to the aspects of the present invention, an image, in which a color difference between a normal part and an abnormal part in an object is enhanced and vascular visibility of the object is improved, can be obtained.

BRIEF DESCRIPTION OF THE DRAWINGS

The above and other objects and advantages of the present invention will be more apparent from the following detailed description of the preferred embodiments when read in connection with the accompanied drawings, wherein like reference numerals designate like or corresponding parts throughout the several views, and wherein.

Figure 3:
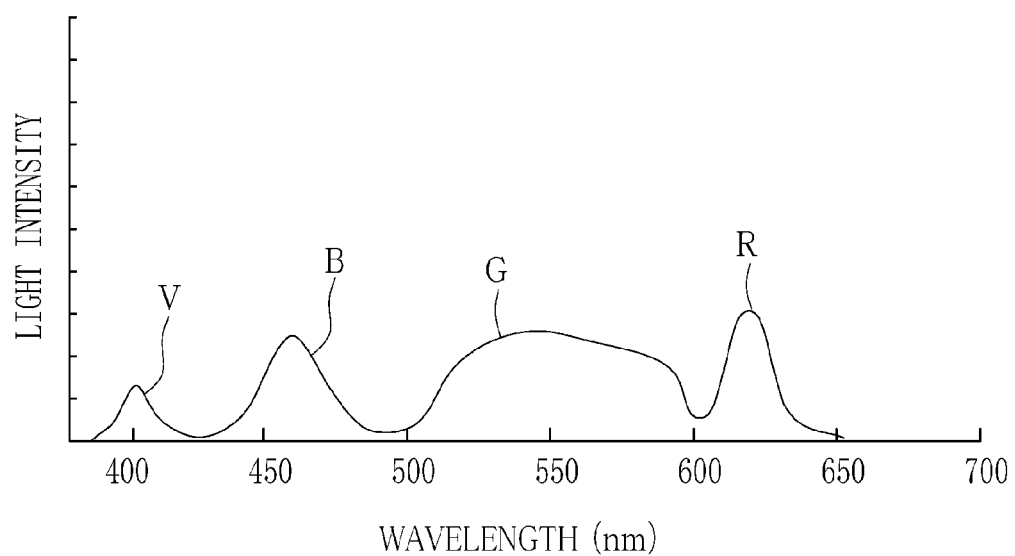
FIG. 3 is a graph illustrating emission spectra of violet light V, blue light B, green light G, and red light R.
Figure 9:
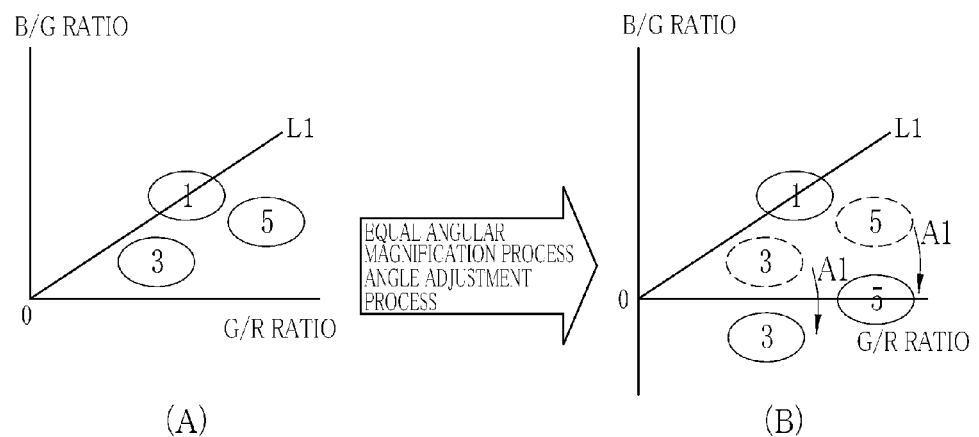
Figure 10:
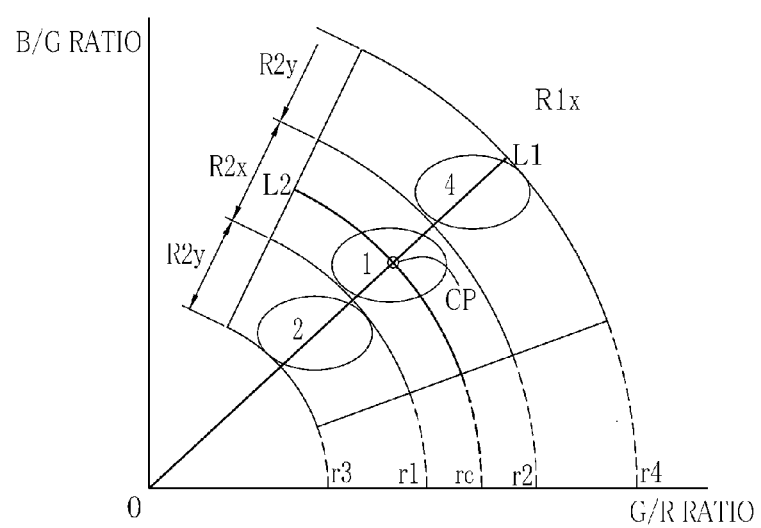
Figure 11:
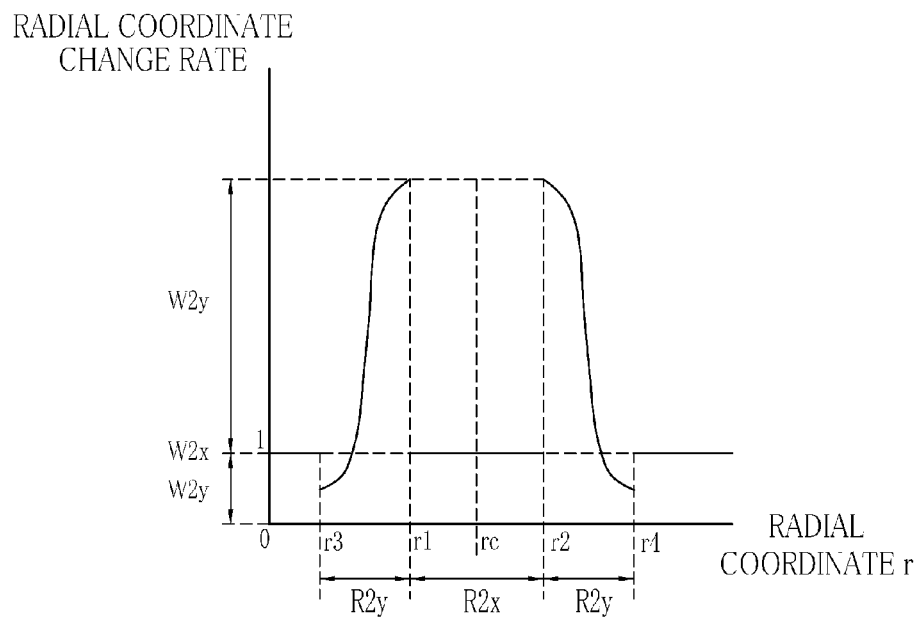
Figure 12:
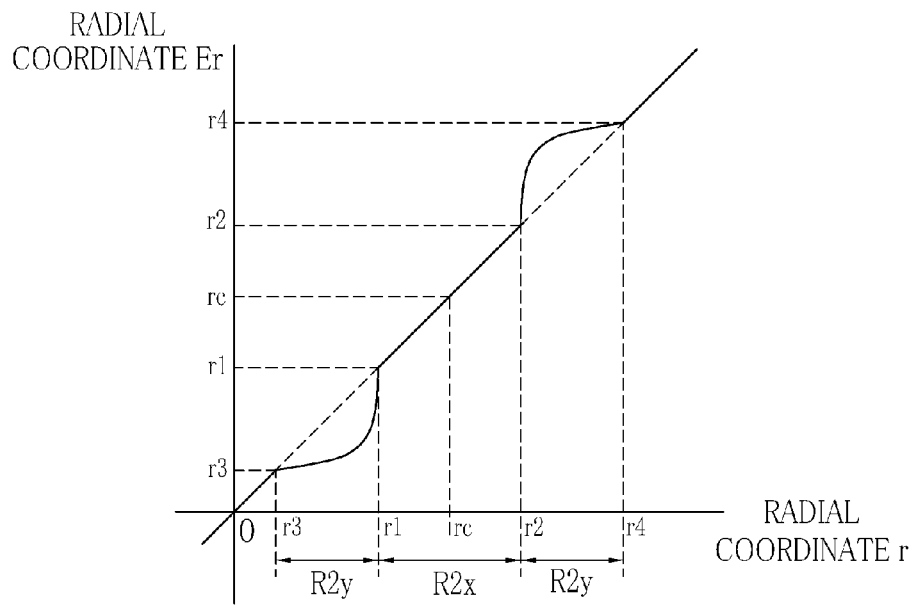
Figure 13:
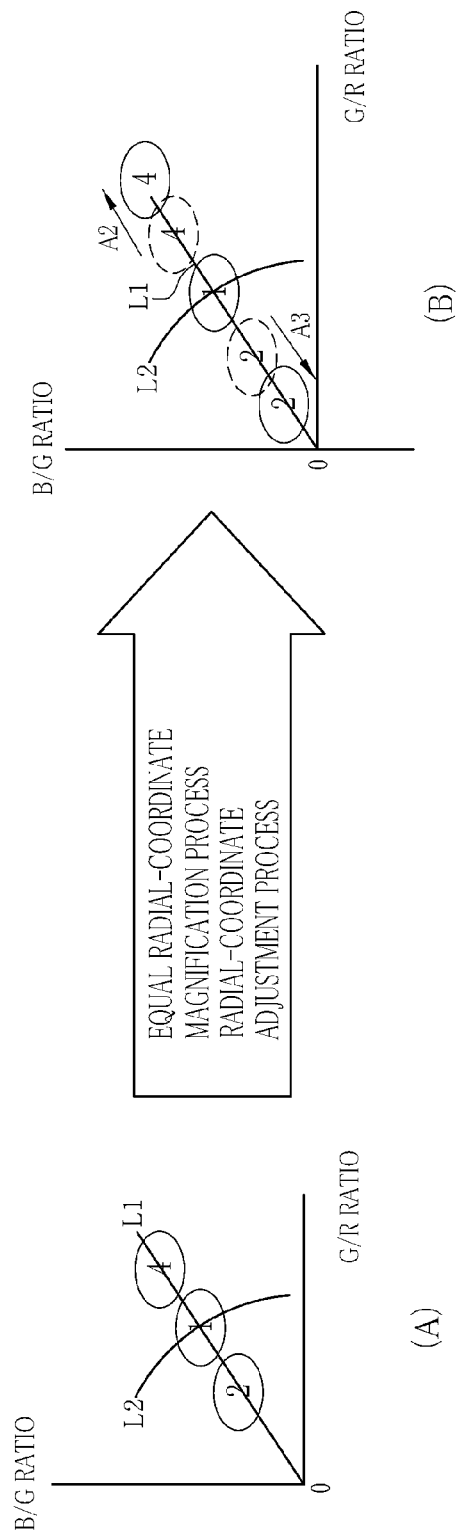
Figure 14:
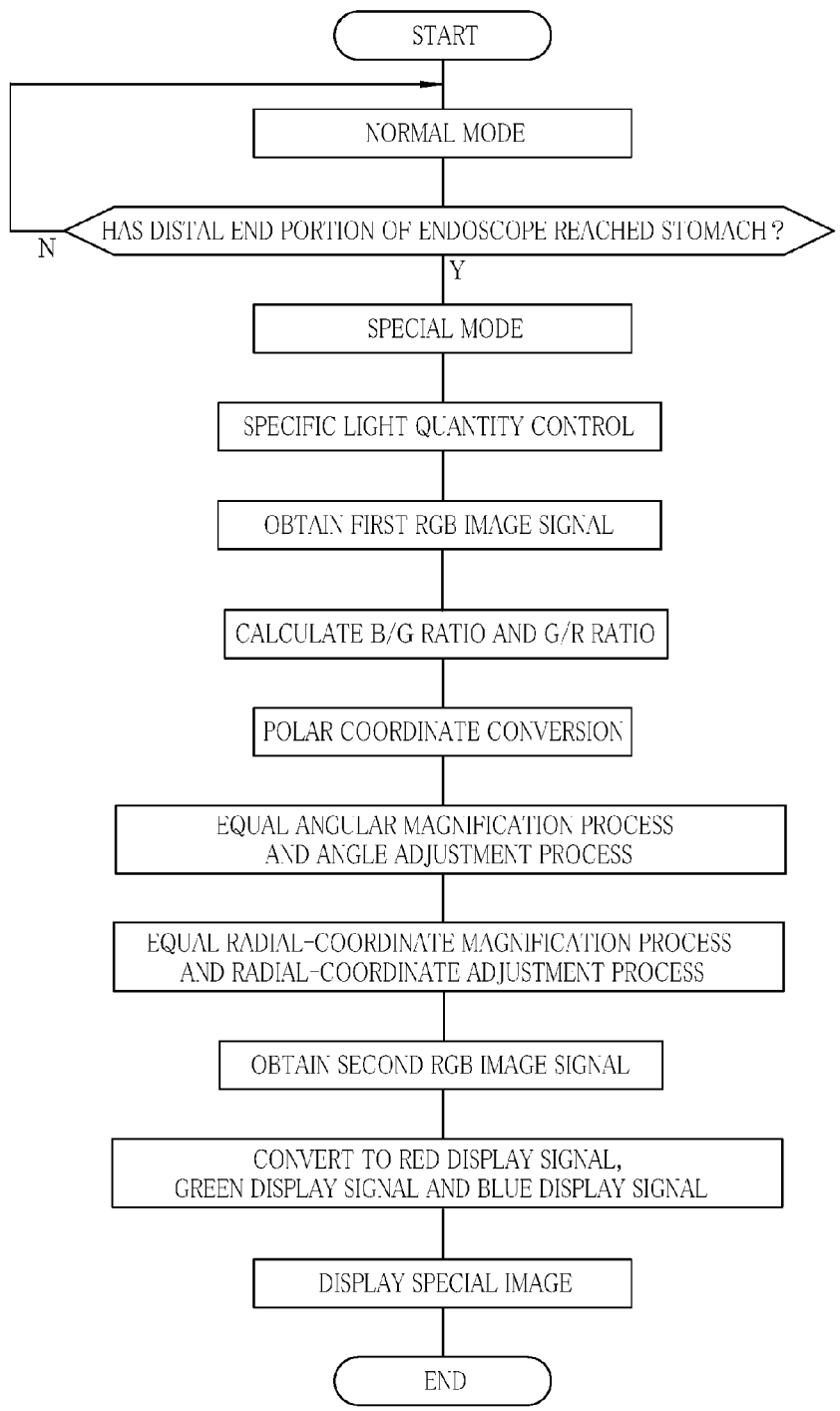
Figure 15:
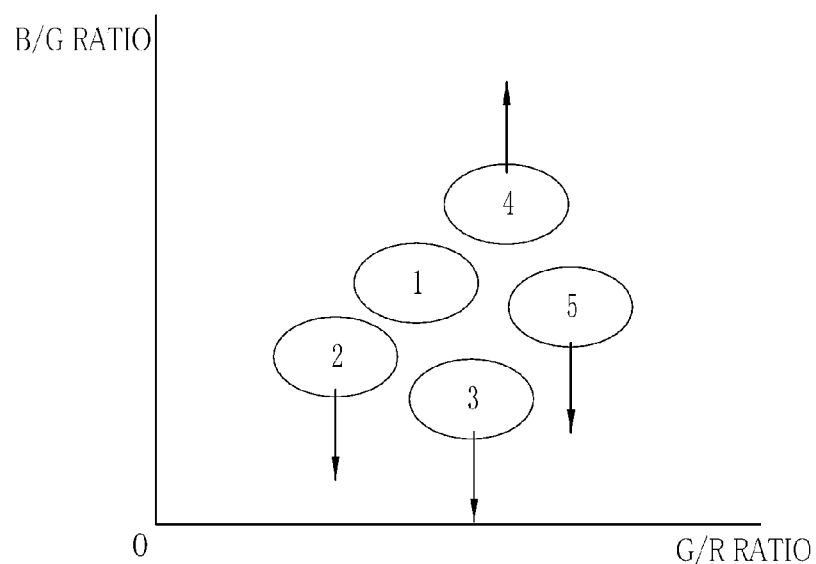
Figure 16:
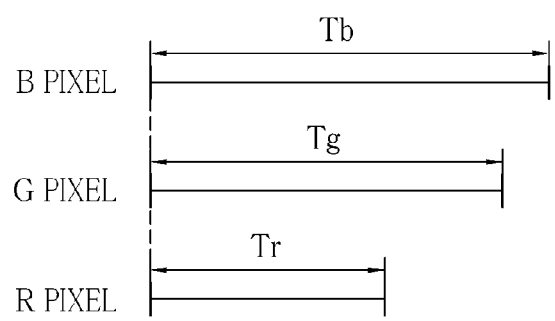
Figure 17:
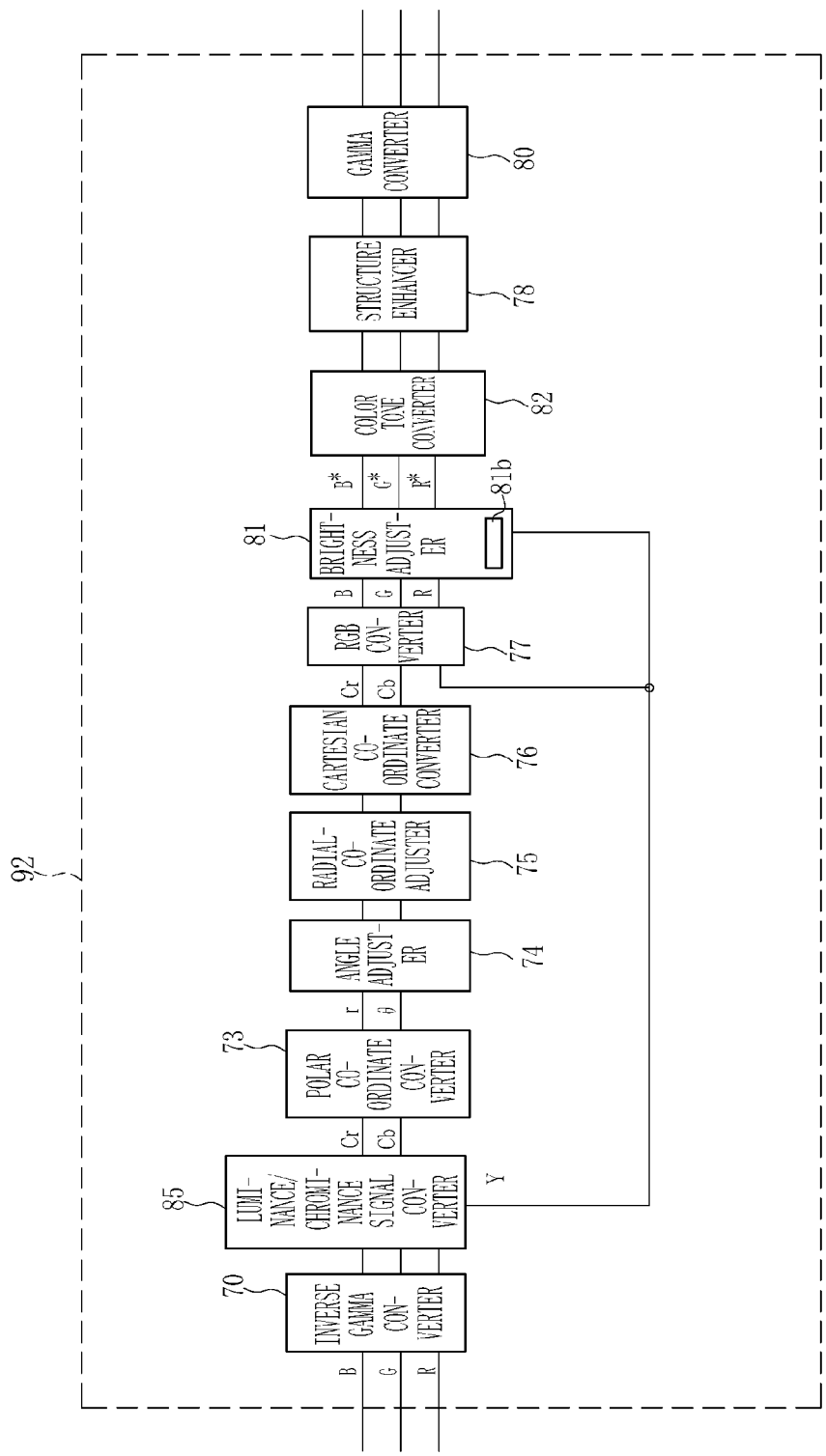
Figure 18:
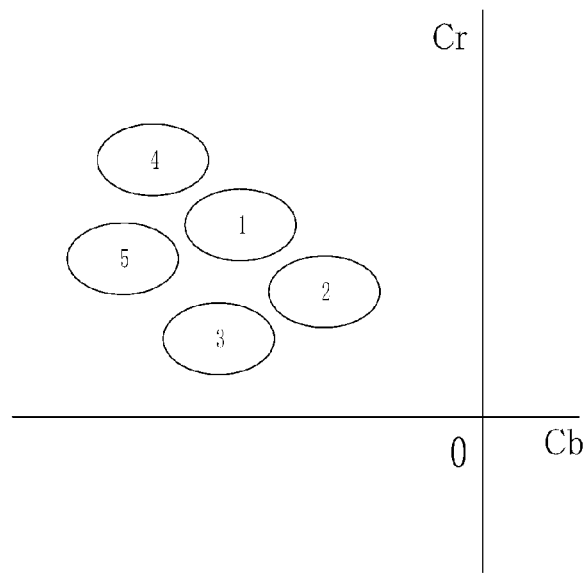
Figure 19:
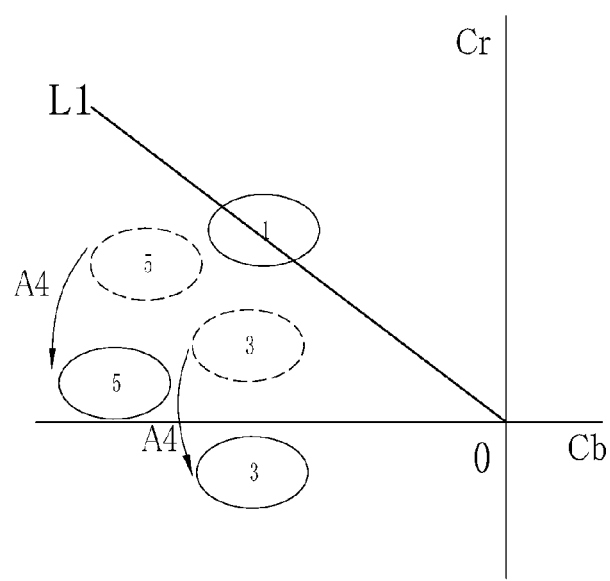
Figure 20:
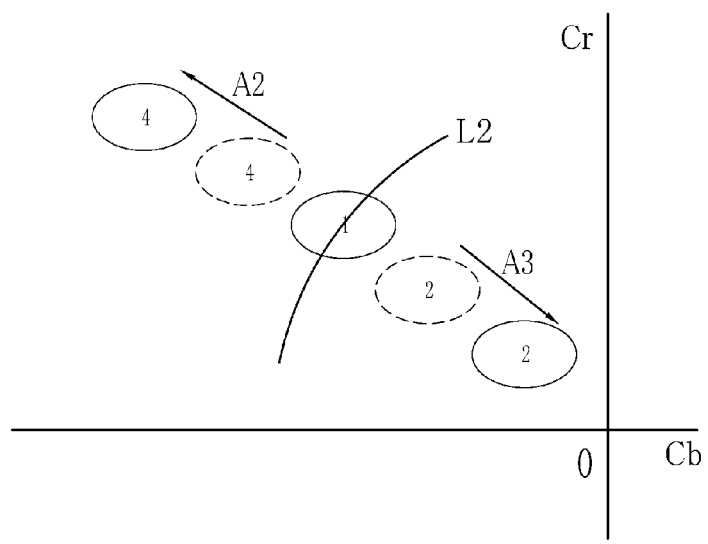
Figure 21:
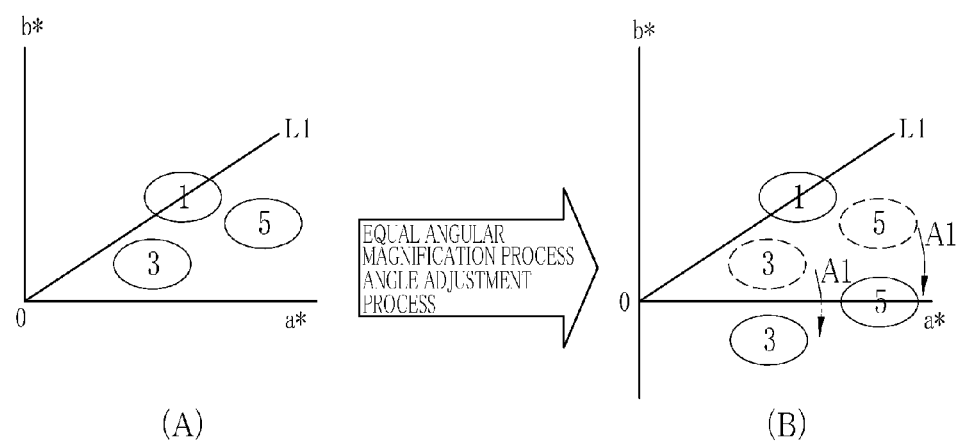
Figure 22:
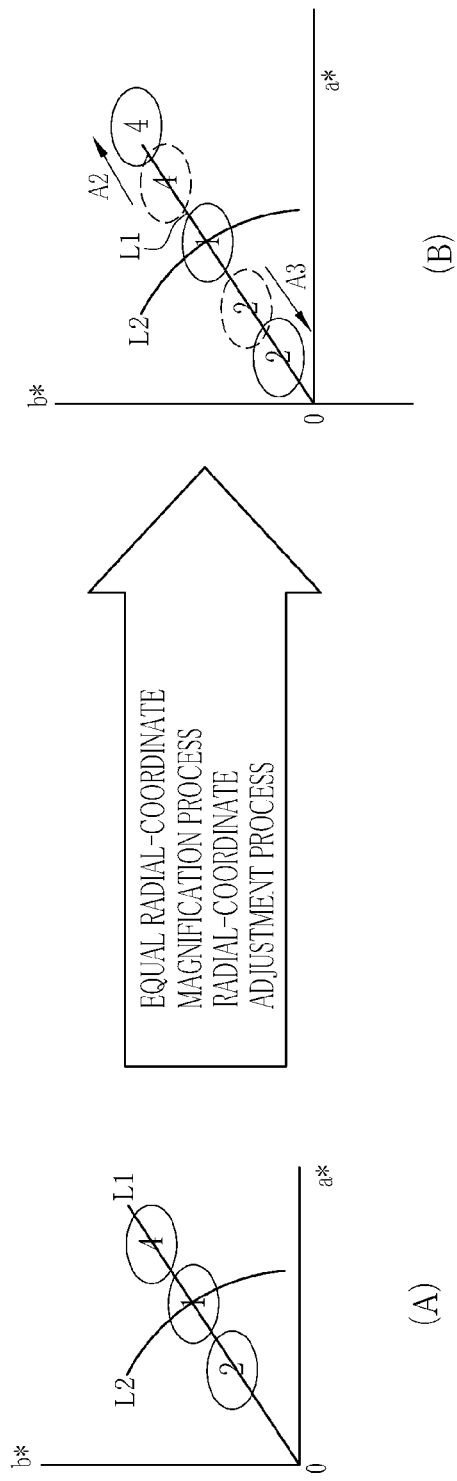
Figure 23:
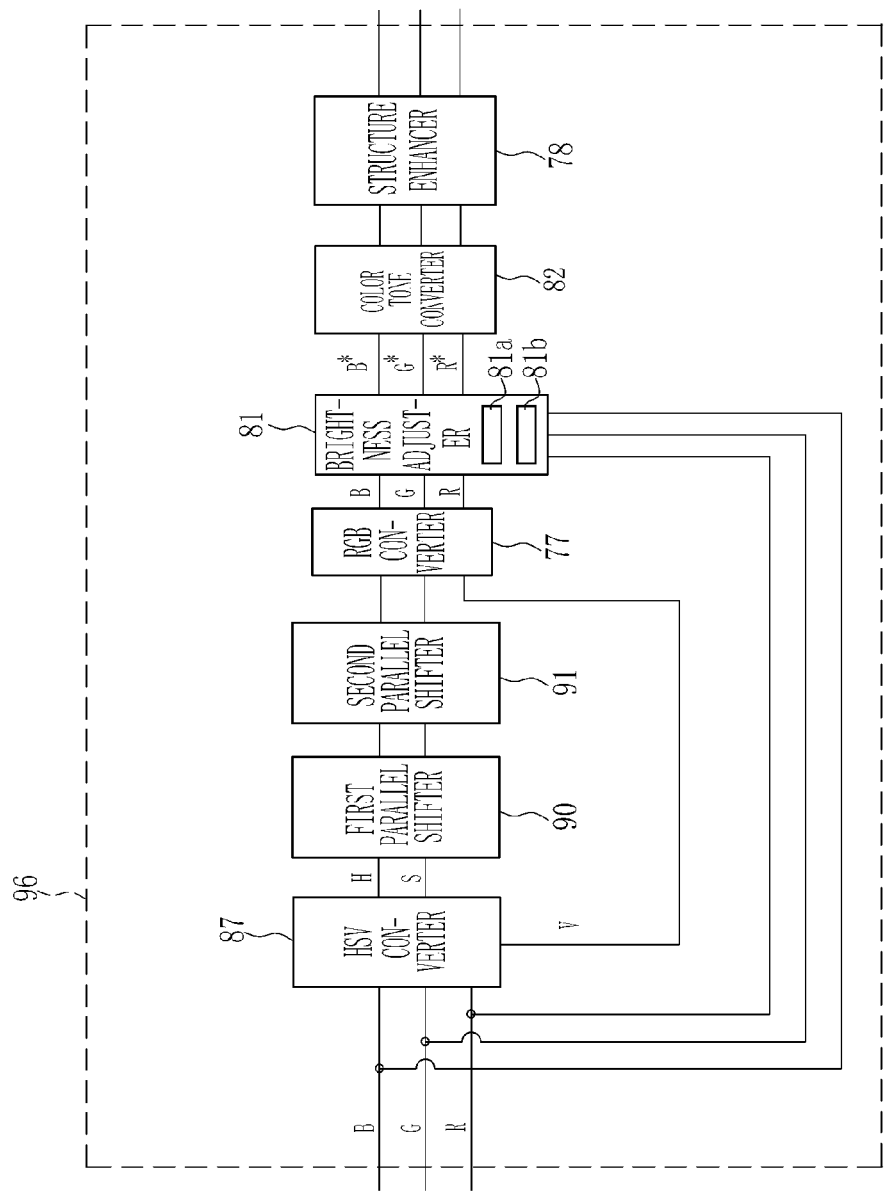
Figure 24:
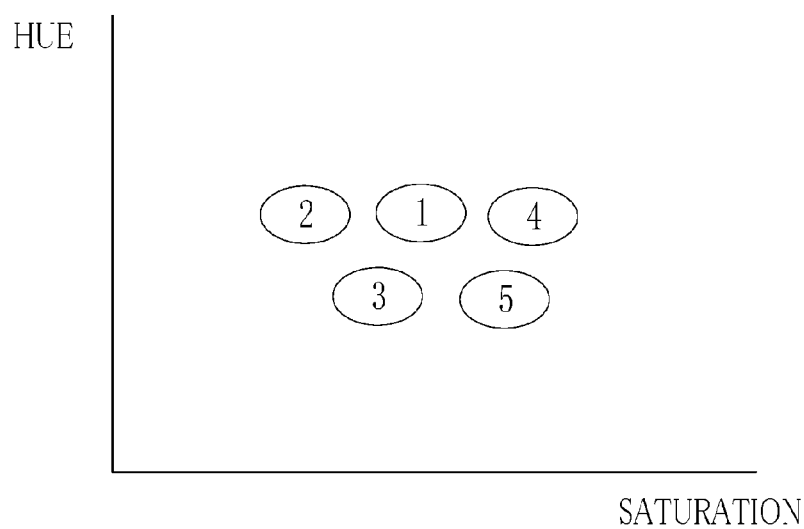
Figure 25:
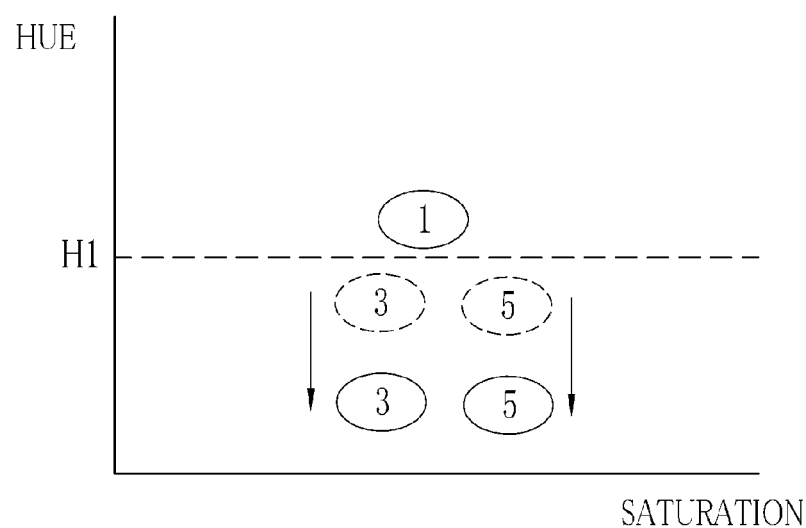
Figure 26:
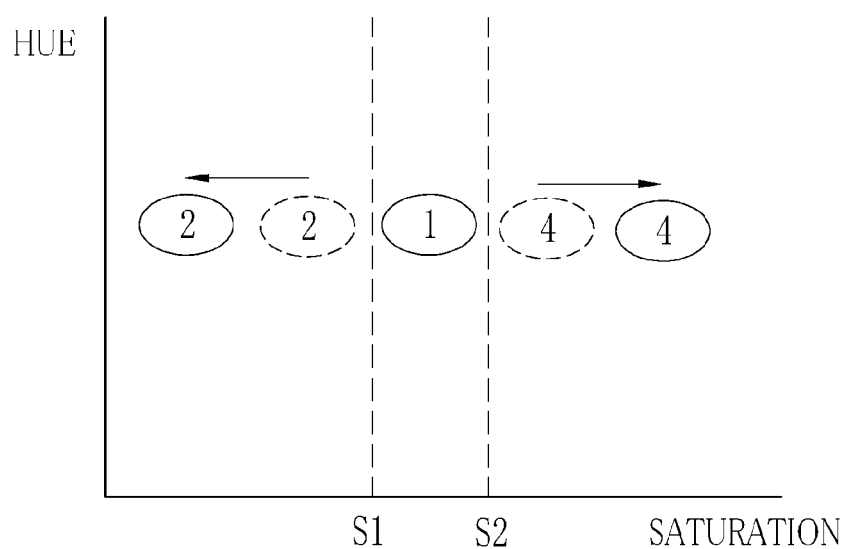
Figure 27:
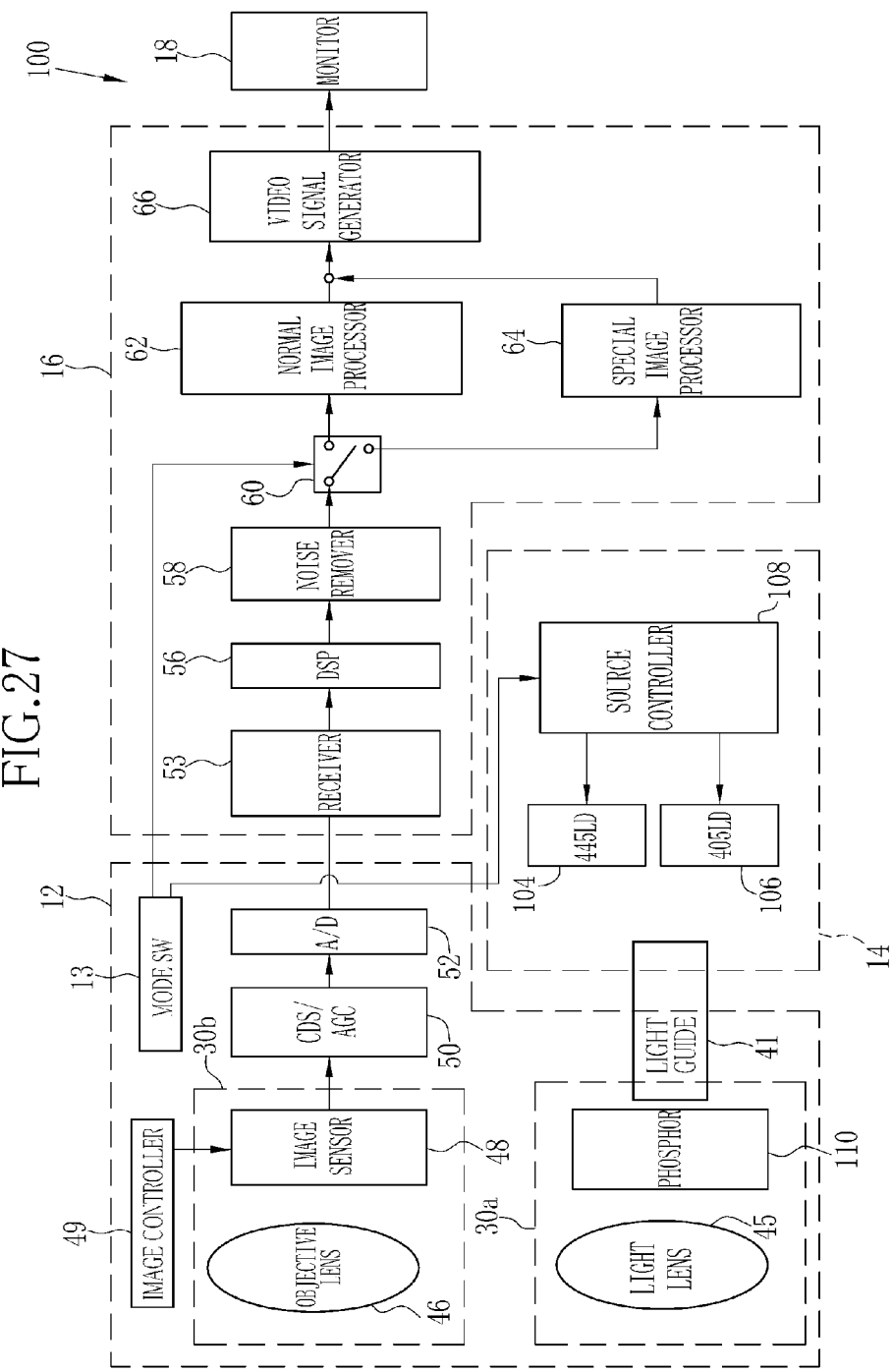
Figure 28:
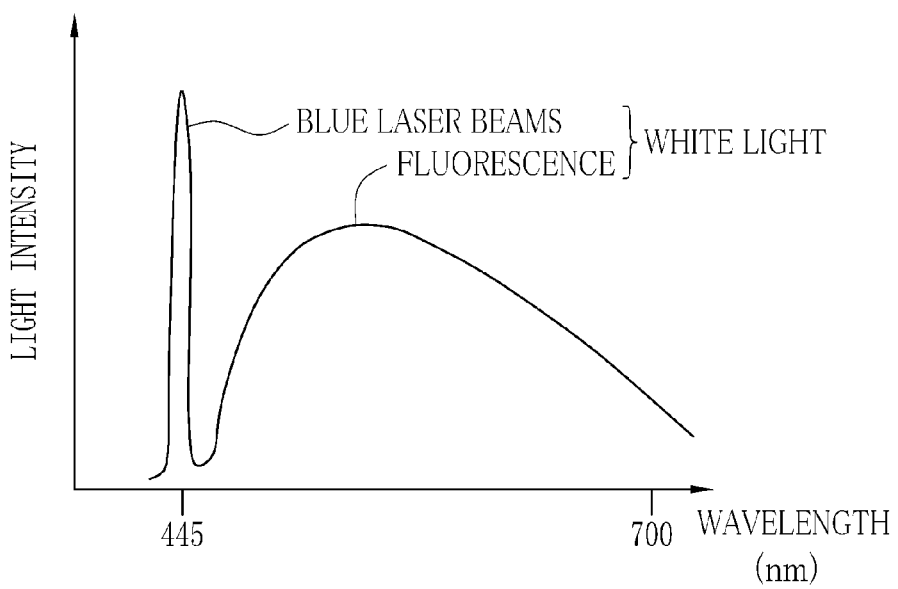
Figure 29:
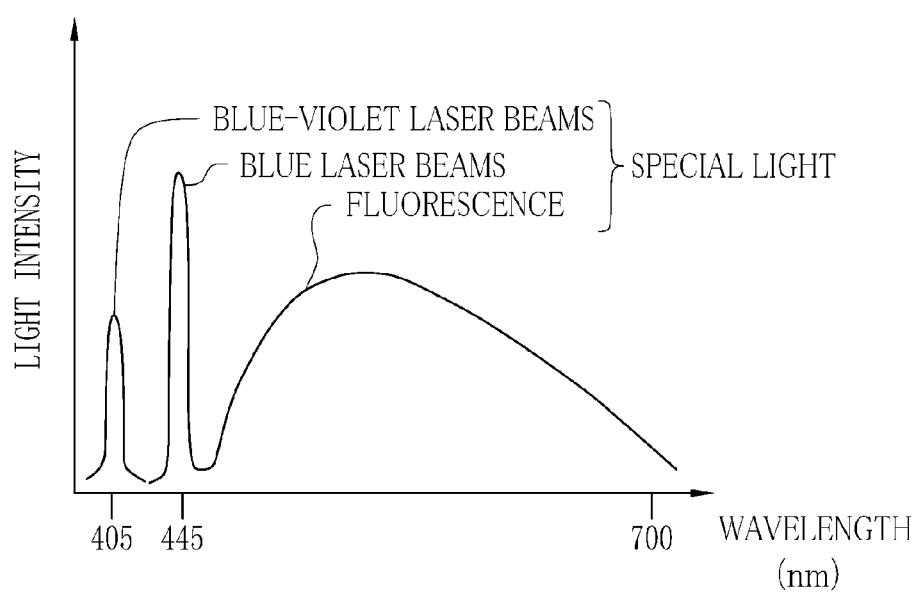
Figure 30:
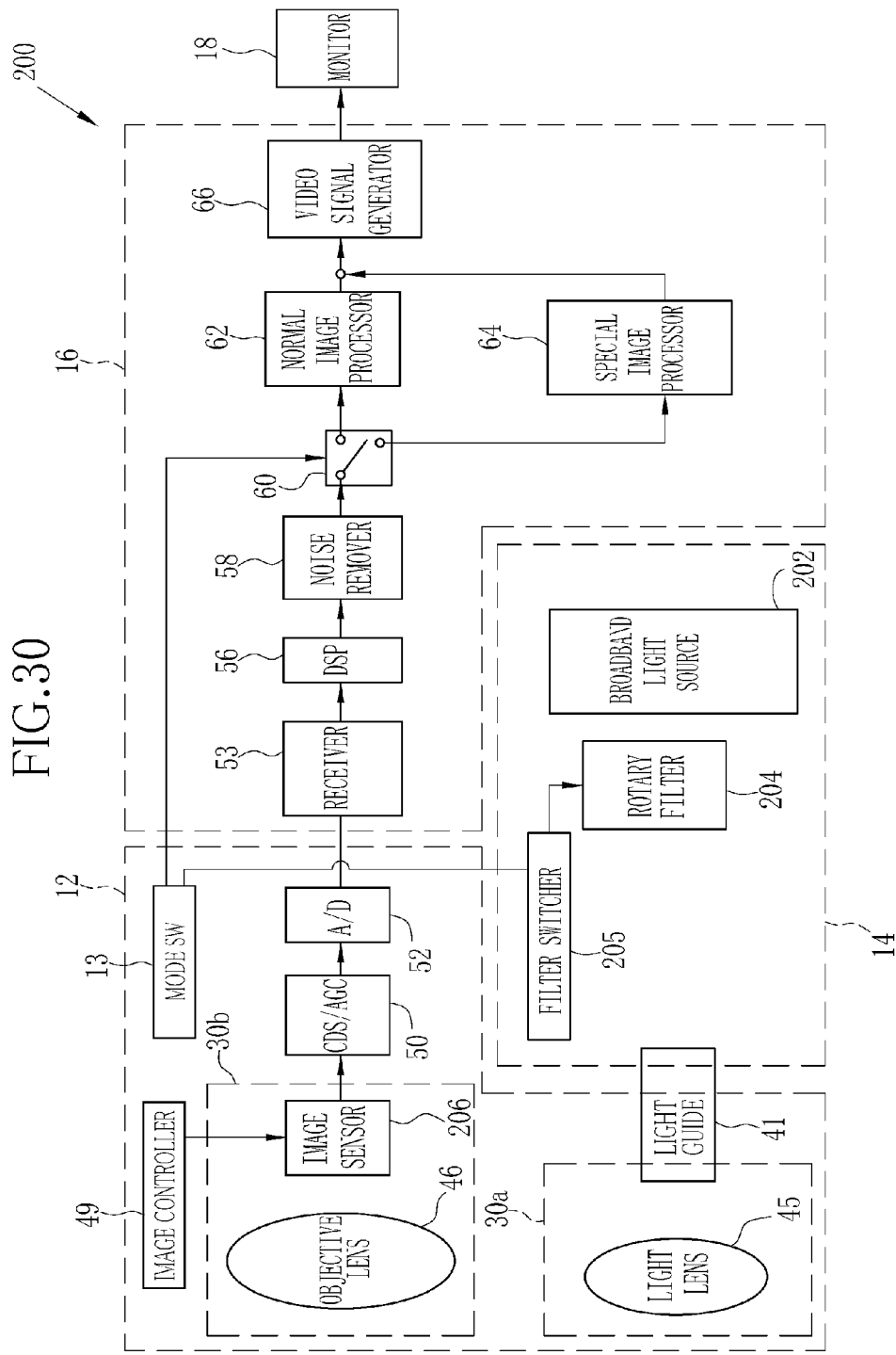
Figure 31:
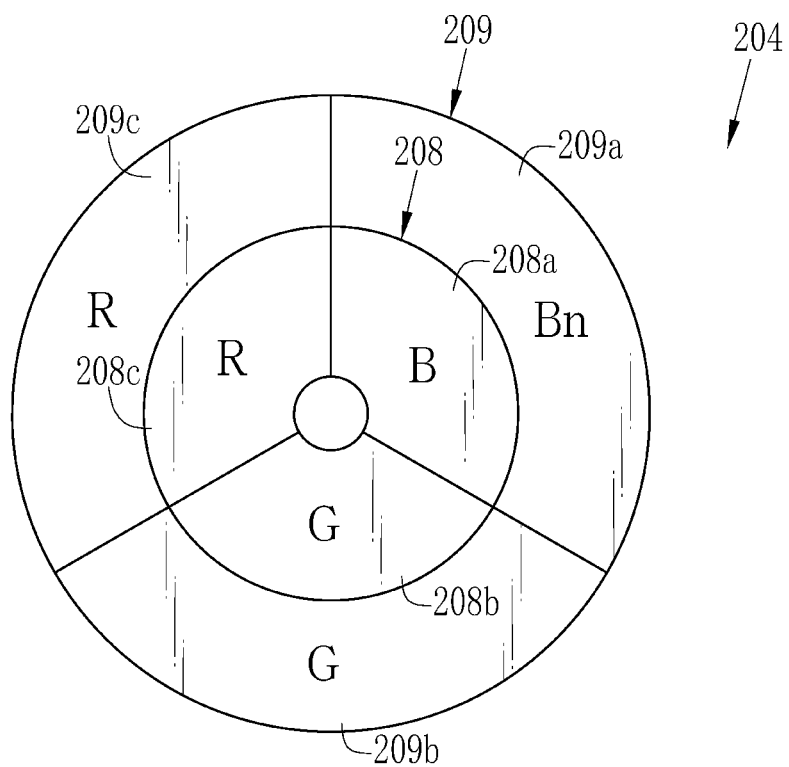
Figure 32:
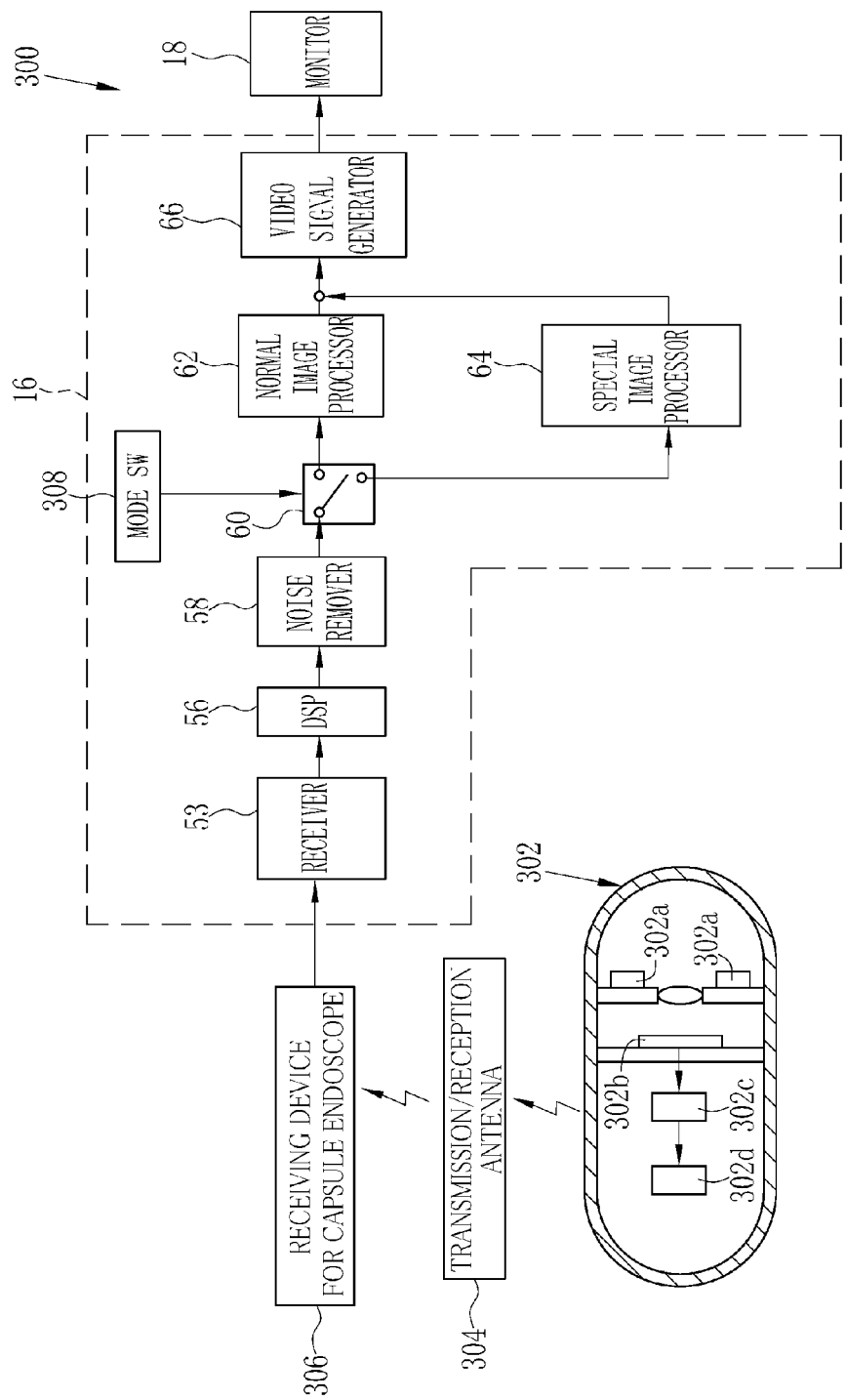
Figure 33:
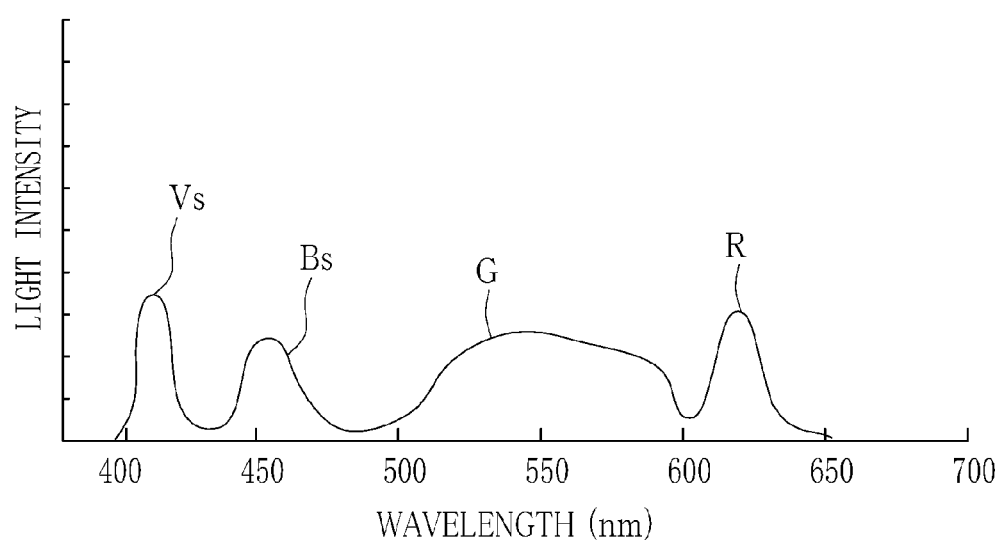
Figure 34:
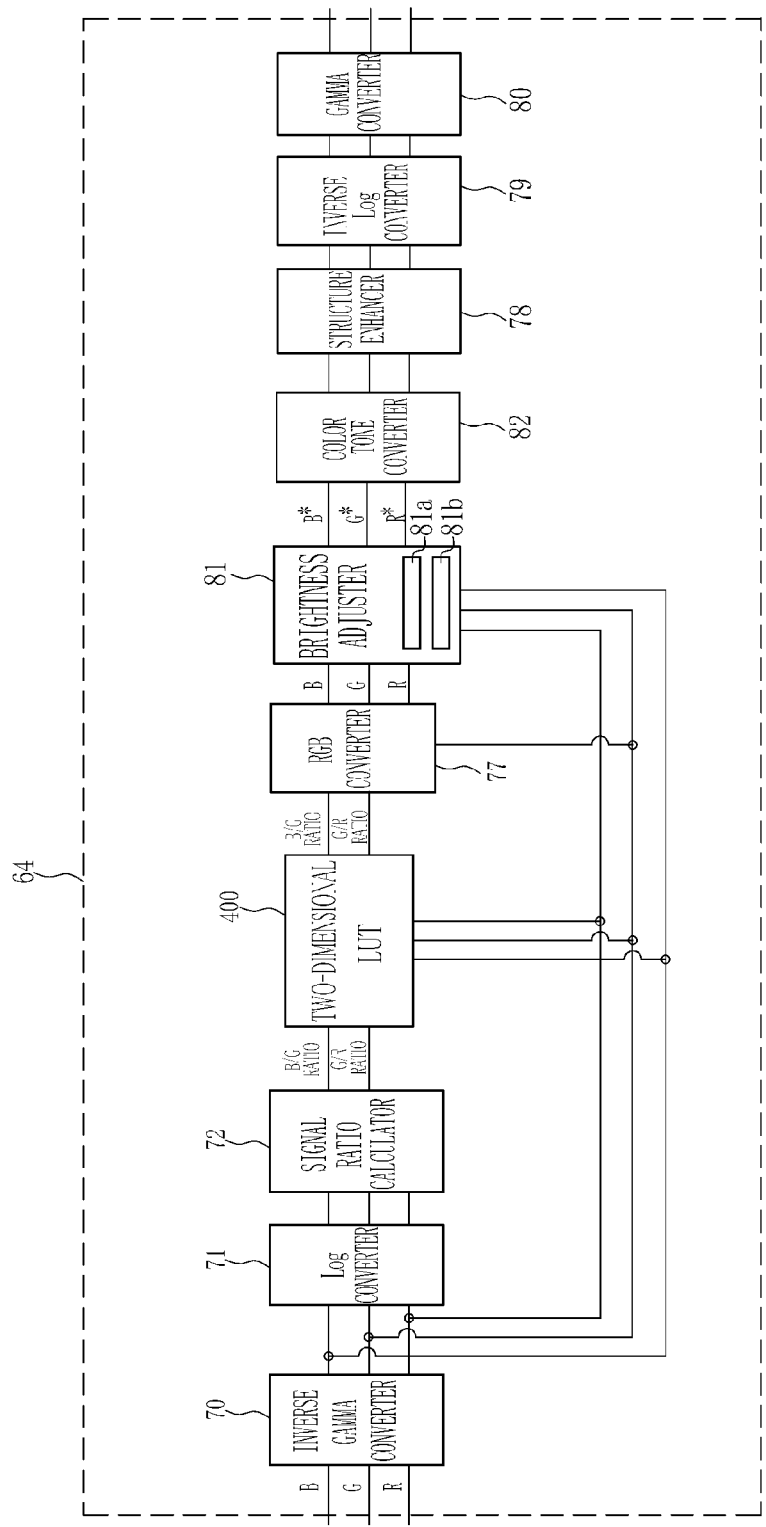

Part (A) of FIG. 9 is an explanatory view illustrating a state before an equal angular magnification process and an angle adjustment process for the signal ratio space, and part (B) of FIG. 9 is an explanatory view illustrating a state after the equal angular magnification process and the angle adjustment process for the signal ratio space;

FIG. 10 is an explanatory view illustrating how to adjust a radial coordinate r;

FIG. 11 is a graph illustrating a relationship between radial coordinate r and radial-coordinate change rate;

FIG. 12 is a graph illustrating a relationship between radial coordinates r and Er;

Part (A) of FIG. 13 is an explanatory view illustrating a state before an equal radial-coordinate magnification process and a radial-coordinate adjustment process for the signal ratio space, and part (B) of FIG. 13 is an explanatory view illustrating a state after the equal radial-coordinate magnification process and the radial-coordinate adjustment process for the signal ratio space;

FIG. 14 is a flowchart illustrating a procedure of observation of the object in a special mode;

FIG. 15 is an explanatory view illustrating shift directions of movement of the second color range, the third color range, the fourth color range and the fifth color range in the signal ratio space;

FIG. 16 is an explanatory view illustrating the accumulation of charge time for BGR picture element of the imaging sensor, FIG. 17 is a block diagram illustrating functions of a special image processor in a case where the feature space is Cb-Cr space;

FIG. 18 is an explanatory view illustrating a distribution of the first color range, the second color range, the third color range, the fourth color range and the fifth color range in the feature space (Cb-Cr space);

FIG. 19 is an explanatory view illustrating a distribution of the first color range, the third color range and the fifth color range before and after the equal angular magnification process and the angle adjustment process for the Cb-Cr space;

FIG. 20 is an explanatory view illustrating a distribution of the first color range, the second color range and the fourth color range before and after the equal radial-coordinate magnification process and the radial-coordinate adjustment process for the Cb-Cr space;

Part (A) of FIG. 21 is an explanatory view illustrating a state before an equal angular magnification process and an angle adjustment process for the ab space and part (B) of FIG. 21 is an explanatory view illustrating a state after the equal angular magnification process and the angle adjustment process for the ab space;

Part (A) of FIG. 22 is an explanatory view illustrating a state before an equal radial-coordinate magnification process and a radial-coordinate adjustment process for the ab space and part (B) of FIG. 22 is an explanatory view illustrating a state after the equal radial-coordinate magnification process and the radial-coordinate adjustment process for the ab space;

FIG. 23 is a block diagram illustrating functions of a special image processor in a case where the feature space is HS space;

FIG. 24 is an explanatory view illustrating a distribution of the first color range, the second color range, the third color range, the fourth color range and the fifth color range in the feature space (HS space);

FIG. 25 is an explanatory view illustrating a parallel shift process by a first parallel shifter;

FIG. 26 is an explanatory view illustrating a parallel shift process by a second parallel shifter;

FIG. 27 is a block diagram illustrating functions of an endoscope system according to Embodiment 2;

FIG. 28 is a graph illustrating an emission spectrum of white light;

FIG. 29 is a graph illustrating an emission spectrum of special light;

FIG. 30 is a block diagram illustrating functions of an endoscope system according to Embodiment 3;

FIG. 31 is a plan view illustrating a rotary filter;

FIG. 32 illustrates functions of a capsule endoscope system according to Embodiment 4;

FIG. 33 is a graph illustrating emission spectra of violet light V, blue light B, green light G, and red light R that are different from those of FIG. 3; and FIG. 34 is a block diagram illustrating functions of the special image processor in a case where a two-dimensional LUT is used.

DESCRIPTION OF THE PREFERRED EMBODIMENTS

Embodiment 1A

Figure 1:
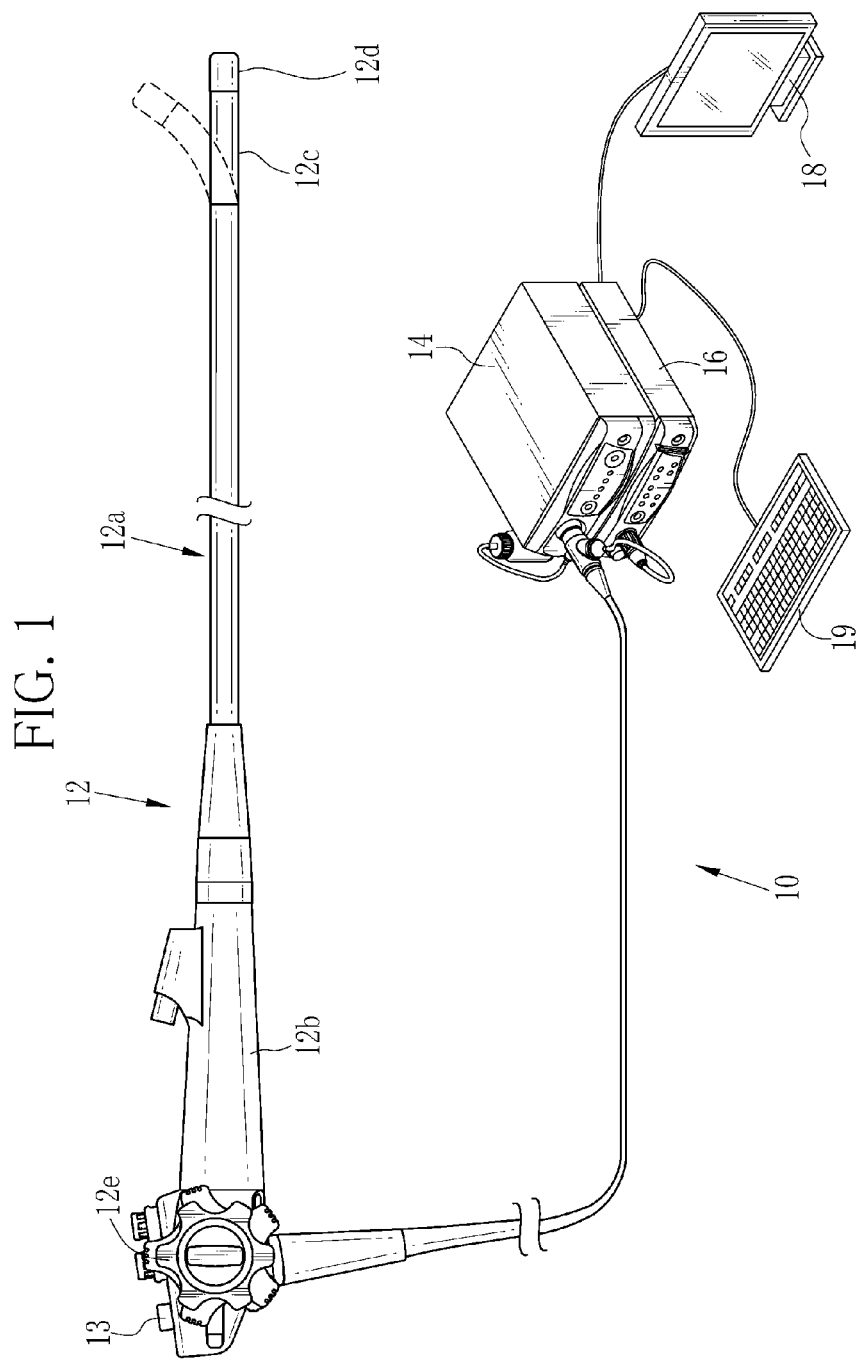
FIG. 1 is an external view of an endoscope of Embodiment 1A.

In FIG. 1, an endoscope system 10 according to an embodiment 1A comprises an endoscope 12, a light source device 14, a processor device 16, a monitor 18, and a console 19. The endoscope 12 is connected optically to the light source device 14 and electrically to the processor device 16. The endoscope 12 comprises an insertion section 12a to be inserted into a body cavity, a control handle unit 12b provided at the proximal end of the insertion section 12a, a flexible portion 12c provided on the distal side of the insertion section 12a, and a distal end portion 12d coupled to the flexible portion 12c. The flexible portion 12c is bent by operating an angle knob 12e of the control handle unit 12b. Thereby the distal end portion 12d is directed to a desired direction.

The control handle unit 12b is provided with the angle knob 12e and a mode switch (SW) 13. The mode SW 13 is operated to switch between a normal mode and a special mode. In the normal mode, a normal image is displayed on the monitor 18. In the special mode, a special image, which emphasizes a color difference between a normal part and an abnormal part in an object and improves vascular visibility, is displayed on the monitor 18.

The processor device 16 is electrically connected to the monitor 18 and the console 19. The monitor 18 displays image information and so on. The console 19 functions as a UI (user interface), which receives an input operation such as setting a function. Note that an external storage unit (not shown) for recording the image information and so on may be connected to the processor device 16.

Figure 2:
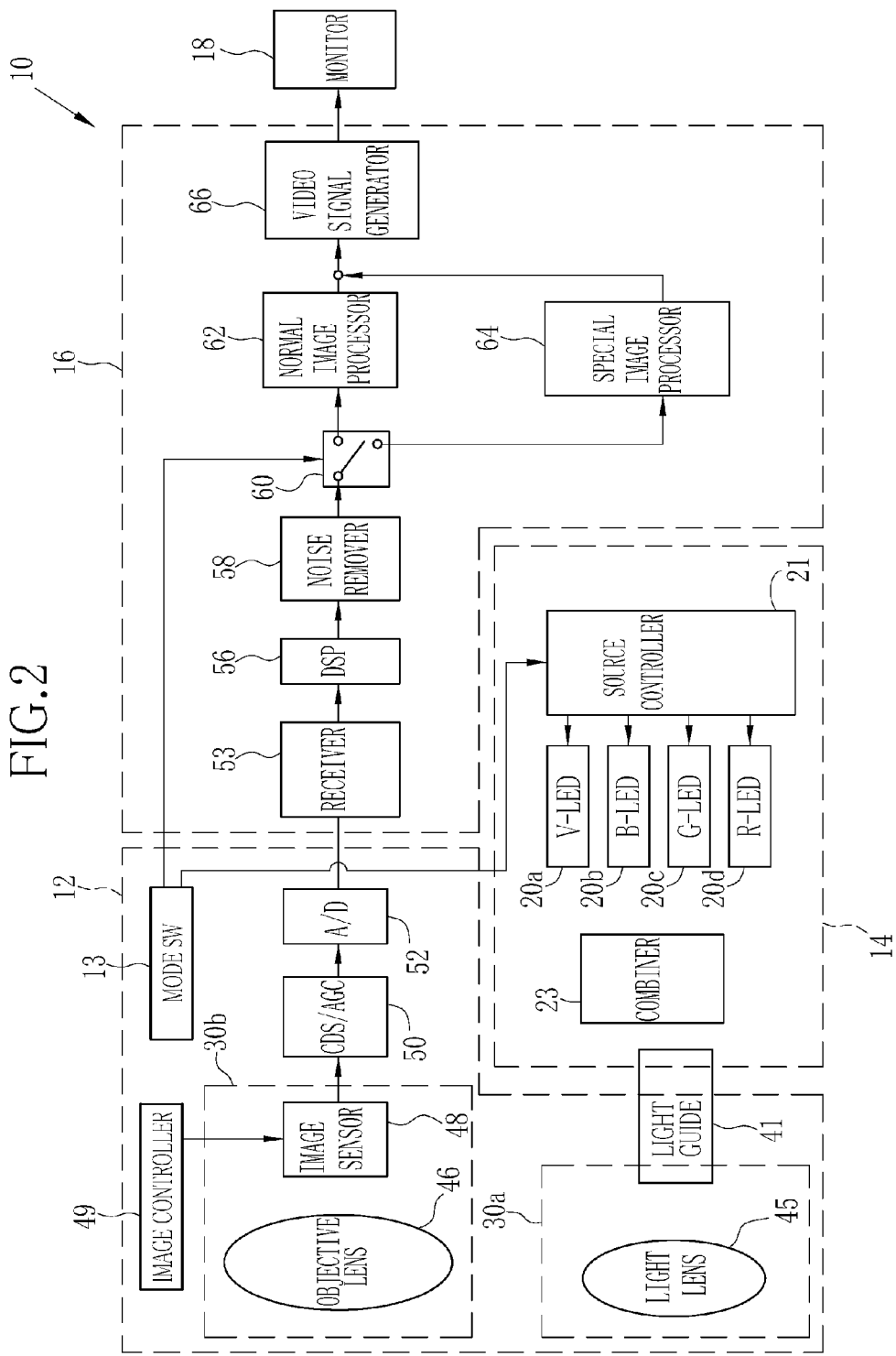
FIG. 2 is a block diagram illustrating functions of the endoscope of Embodiment 1A.

As illustrated in FIG. 2, the light source device 14 comprises a V-LED (Violet Light Emitting Diode) 20a, a B-LED (Blue Light Emitting Diode) 20b, a G-LED (Green Light Emitting Diode) 20c, an R-LED (Red Light Emitting Diode) 20d, a source controller 21 for controlling the LEDs 20a to 20d, and a combiner 23. The combiner 23 combines the optical paths of four colors of light from the four colors of LEDs 20a to 20d together. The light combined by the combiner 23 is applied to the object in a body cavity through a light guide (LG) 41 and a light lens 45. The light guide 41 extends inside the insertion section 12a. Note that an LD (Laser Diode) may be used in place of the LED. In addition, "the light source" of the present invention corresponds to a configuration having at least the V-LED 20a, the G-LED 20c and the R-LED 20d.

As illustrated in FIG. 3, the V-LED 20a generates violet light V having a wavelength range of 380 to 420 nm and the center wavelength of 405±10 nm. The B-LED 20b generates blue light B having a wavelength range of 420 to 500 nm and the center wavelength of 460±10 nm. The G-LED 20c generates green light G having a wavelength range of 480 to 600 nm. The R-LED 20d generates red light R having a wavelength range of 600 to 650 nm and the center wavelength in a range of 620 to 630 nm. In addition, the peak wavelength may be the same as or different from the center wavelength of the each color light.

In each of the normal mode and the special mode, the source controller 21 turns on the V-LED 20a, the B-LED 20b, the G-LED 20c, and the R-LED 20d. Accordingly, the mixture of the violet light V, the blue light B, the green light G, and the red light R is applied to the object. The source controller 21 sets a light quantity ratio among the violet light V, the blue light B, the green light G, and the red light R to be different between the normal mode and the special mode. In the normal mode, the source controller 21 controls the LEDs 20a to 20d so that a light quantity ratio among the violet light V, the blue light B, the green light G, and the red light R is set to Vc:Bc:Gc:Rc.

In the special mode, the source controller 21 controls the LEDs 20a to 20d so that the light quantity ratio among the violet light V, the blue light B, the green light G, and the red light R is set to Vs:Bs:Gs:Rs. It is different between Vc and Vs, Bc and Bs, Gc and Gs, and Rc and Rs. In the special mode, the source controller 21 may execute a specific light quantity control which makes the quantity of the violet light V and the green light G larger than the quantity of the red light R. To generate the special image to be displayed on the monitor 18 in the special mode, as described later, B image signal obtained by imaging of the object based on the violet light V and the blue light B, and G image signal obtained by imaging of the object based on the green light G are used, but R image signal obtained by imaging of the object based on the red light R is not used.

Therefore, to make the sensibility of the B image signal and the G image signal higher than the sensitivity of the R image signal, the specific light quantity control makes the quantities of the violet light V affecting the B image signal and the green light G affecting the G image signal larger than the quantity of the red light R affecting the R image signal. Accordingly, the special image can be displayed, in which a color difference between the normal part and the abnormal part in the object becomes larger and vascular visibility is more improved in comparison with a case not to perform the specific light quantity control. Note that the specific light quantity control may further perform a control to make the quantity of the blue light B larger than the quantity of the red light R.

As illustrated in FIG. 2, the light guide 41 is incorporated in the endoscope 12 and a universal code that connects the endoscope 12, the light source device 14, and the processor device 16. The light guide 41 transmits the light combined by the combiner 23 to the distal end portion 12d of the endoscope 12. Note that a multimode fiber may be used as the light guide 41. For example, a small-diameter fiber cable with the core diameter 105 μm, the clad diameter 125 μm, and the outer diameter φ 0.3 to 0.5 mm (including a protection layer, which is a jacket) may be used. Also, a fiber cable which bundled up small-diameter fibers of φ 0.03 mm may be used.

The distal end portion 12d of the endoscope 12 comprises an illumination optical system 30a and an imaging optical system 30b. The illumination optical system 30a has the light lens 45. The light from the light guide 41 is applied to the object through the light lens 45. The imaging optical system 30b has an objective lens 46 and an image sensor 48. The light reflected from the object is incident on the image sensor 48 through the objective lens 46. Thereby a reflection image of the object is formed on the image sensor 48.

The image sensor 48 is a color image sensor, which captures the reflection image of the object and outputs an image signal according to controls from an image controller 49. It is preferred that the image sensor 48 is a CCD (Charge Coupled Device) image sensor, a CMOS (Complementary Metal-Oxide Semiconductor) image sensor, or the like. The image sensor 48 used in the embodiments of the present invention is a color image sensor that obtains image signals of three colors, R (red), G (green), and B (blue), that is, a so-called RGB image sensor comprising R pixels (corresponding to red pixels of the present invention) with R filters, G pixels (corresponding to green pixels of the present invention) with G filters, and B pixels (corresponding to blue pixels of the present invention) with B filters.

Note that the image sensor 48 may be a so-called complementary color image sensor instead of the RGB image sensor. The complementary color image sensor has complementary color filters of C (cyan), M (magenta), Y (yellow), and G (green). In case the complementary color image sensor is used, four colors (CMYG) of image signals are outputted. It is necessary to convert the four colors (CMYG) of image signals into three colors (RGB) of image signals through complementary color/primary color conversion. Alternatively, the image sensor 48 may be a monochrome image sensor with no color filters. In this case, it is necessary that the source controller 21 allows emitting the blue light B, the green light G, and the red light R in a time-division manner. It is also necessary to add a synchronization process in processing the image signals.

The image signal output from the image sensor 48 is transmitted to a CDS/AGC circuit 50. The CDS/AGC circuit 50 performs correlated double sampling (CDS) and automatic gain control (AGC) on the image signal that is an analog signal. The image signal that has passed through the CDS/AGC circuit 50 is converted into a digital image signal by an A/D converter 52. The A/D converted digital image signal is inputted to the processor device 16.

The processor device 16 comprises an input processor 53, a DSP (Digital Signal Processor) 56, a noise reducer 58, an image processing selector 60, a normal image processor 62, a special image processor 64, and a video signal generator 66. The input processor 53 performs an input process of the digital RGB image signals from the endoscope 12 and outputs the image signals to the DSP 56. The R image signal corresponds to the signals outputted from the R pixels of the image sensor 48. The G image signal corresponds to the signals outputted from the G pixels of the image sensor 48. The B image signal corresponds to the signals outputted from the B pixels of the image sensor 48.

The DSP 56 applies various types of signal processes such as a defect correction process, an offset process, a gain correction process, a linear matrix process, a gamma conversion process, a demosaic process and so on to the image signal received. In the defect correction process, signals from defective pixels in the image sensor 48 are corrected. In the offset process, dark current components are removed from the RGB image signals which have been subjected to the defect correction process. Thereby an accurate zero level is prescribed. In the gain correction process performed after the offset process, a signal level is adjusted or corrected by multiplying the RGB image signals by a specific gain. After the gain correction process, the RGB image signals are subjected to the linear matrix process to increase color reproducibility. Thereafter, brightness and saturation are adjusted or corrected through the gamma conversion process. After the linear matrix process, the RGB image signals are subjected to the demosaic process (also referred to as equalization process) in which a color signal lacking in each pixel is generated by interpolation. Owing to the demosaic process, each pixel has three colors (RGB) of signals.

After the DSP 56 applies the gamma correction and so on to the RGB image signals, the noise reducer 58 reduces noise from the RGB image signals through a noise reducing process (for example, a moving average method or a median filter method). The RGB image signals from which the noise has been reduced are transmitted to the image processing selector 60.

In case that the normal mode is set by operating the mode SW 13, the image processing selector 60 transmits the RGB image signals to the normal image processor 62. In case that the special mode is set, the image processing selector 60 transmits the RGB image signals to the special image processor 64.

The normal image processor 62 applies 3×3 matrix processing, tone conversion process, three-dimensional LUT process and various types of color enhancement processes for the RGB image signals. The processed RGB image signals are subjected to the structure enhancement process (e.g. spatial frequency enhancement and the like). The structure-enhanced RGB image signals are inputted to the video signal generator 66.

The special image processor 64 generates the special image which emphasizes a color difference between a normal part and an abnormal part in an object and improves vascular visibility, based on the RGB image signals. Details of the special image processor 64 will be described later. The special image processor 64 outputs a red display signal, a green display signal and a blue display signal to display a special image, and these three-color display signals are input into the video signal generator 66.

In case that the normal mode is set, the video signal generator 66 converts the signal input from the normal image processor 62 into a normal video signal which enables a display of the normal image on the monitor 18. The monitor 18 displays the normal image based on the normal video signal. In case that the special mode is set, the video signal generator 66 converts the red display signal, the green display signal and the blue display signal input from the special image processor 64 into a special video signal which enables a display of the special image on the monitor 18. The monitor 18 displays the special image based on the special video signal.

Figure 4:
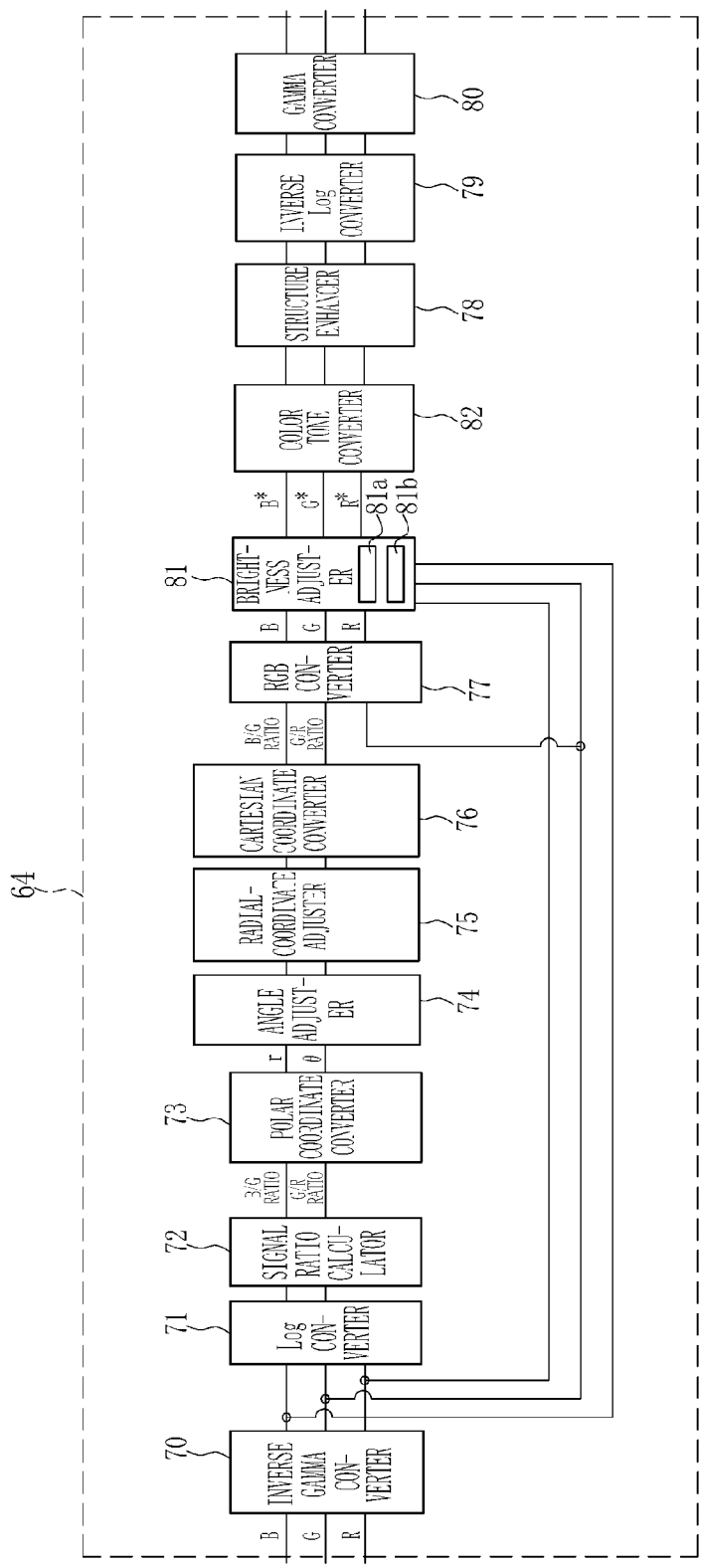
FIG. 4 is a block diagram illustrating functions of a special image processor in a case where the feature space is a signal ratio space.

As illustrated in FIG. 4, the special image processor 64 comprises an inverse gamma converter 70, a log converter 71, a signal ratio calculator 72, a polar coordinate converter 73, an angle adjuster 74, a radial-coordinate adjuster 75, a Cartesian coordinate converter 76, an RGB converter 77, a structure enhancer 78, an inverse log converter 79, and a gamma converter 80. The special image processor 64 also comprises a brightness adjuster 81 and a color tone converter 82 between the RGB converter 77 and the structure enhancer 78.

The inverse gamma converter 70 performs inverse gamma conversion on the inputted digital image signals of the RGB channels. The RGB image signals after the inverse gamma conversion are linearly-changing RGB signals, which change linearly relative to reflectance from the object. Owing to this, a proportion of the signal components related to various types of biological information of the object increases in the RGB image signals. Note that the linearly-changing R image signal is referred to as a first R image signal. The linearly-changing G image signal is referred to as a first G image signal. The linearly-changing B image signal is referred to as a first B image signal.

The log converter 71 performs log conversion of each of the linearly-changing RGB image signals. Thereby, log-converted R image signal (log R) (corresponding to the first red signal of the present invention), log-converted G image signal (log G) (corresponding to the first green signal of the present invention), and log-converted B image signal (log B) (corresponding to the first blue signal of the present invention) are obtained.

The signal ratio calculator 72 (corresponding to the color information obtaining processor of the present invention) performs difference processing (log G−log B=log G/B=−log (B/G)) based on the first G image signal and the first B image signal. Thereby, the B/G ratio is calculated. The B/G ratio refers to −log (B/G) with "−log" omitted. The G/R ratio is calculated by difference processing (log R−log=log R/G=−log (G/R)) based on the first R image signal and the first G image signal. The G/R ratio refers to −log (G/R) with "−log" omitted in a manner similar to the B/G ratio. The G/R ratio refers to −log (G/R) with "−log" omitted in a manner similar to the B/G ratio. Note that in the present invention, "the first signal ratio" corresponds to the B/G ratio, and "the second signal ratio" corresponds to the G/R ratio.

Note that the B/G ratio and the G/R ratio are calculated from the pixel values of the pixels located in the same (or corresponding) positions in the B image signal, the G image signal, and the R image signal. The B/G ratio and the G/R ratio are calculated for each pixel. The B/G ratio correlates with a blood vessel depth (distance between the mucosal surface and a position of a specific blood vessel), so that the B/G ratio varies with the blood vessel depth. The G/R ratio correlates with the blood volume (hemoglobin index), so that the G/R ratio varies with the blood volume.

The polar coordinate converter 73 converts the B/G ratio and the G/R ratio, which are calculated by the signal ratio calculator 72, into a radial coordinate r and an angle θ. The polar coordinate converter 73 performs the conversion into the radial coordinate r and the angle θ for each pixel. In the signal ratio space formed by the B/G ratio and the G/R ratio, the angle adjuster 74 performs an angle adjustment process for changing an angle in the second color range, the third color range, the fourth color range and the fifth color range containing many of the B/G ratios and the G/R ratios corresponding to the abnormal part in the object, without changing an angle in the first color range containing many of the B/G ratios and the G/R ratios corresponding to the normal part in the object, among the plural color ranges where the B/G ratios and the G/R ratios of the object in the body cavity are distributed. Details of the angle adjustment process will be described later. In the signal ratio space, the radial coordinate adjuster 75 performs a radial-coordinate adjustment process for changing a radial coordinate in the second color range, the third color range, the fourth color range and the fifth color range, without changing a radial-coordinate in the first color range. Details of the radial-coordinate adjustment process will be described later.

The Cartesian coordinate converter 76 converts the radial coordinate r and the angle θ, which have passed through the angle adjuster 74 and the radial-coordinate adjuster 75, into Cartesian coordinates. Thereby the radial coordinate r and the angle θ are converted into the B/G and G/R ratios (corresponding to the second color information of the present invention) whose angle θ and radial coordinate r have been adjusted. The RGB converter 77 uses at least one of the first RGB image signals to convert the B/G and G/R ratios whose angle θ and radial coordinate r have been adjusted, into second RGB image signals. To convert the B/G ratio into the second B image signal (corresponding to the second blue signal of the present invention), the RGB converter 77 performs arithmetic operations based on the B/G ratio whose angle θ and radial coordinate r have been adjusted and the first G image signal, for example. To convert the G/R ratio into the second R image signal (corresponding to the second red signal of the present invention), the RGB converter 77 performs arithmetic operations based on the G/R ratio whose angle θ and radial coordinate r have been adjusted and the first G image signal, for example. The RGB converter 77 outputs the first G image signal as the second G image signal (corresponding to the second green signal of the present invention), without any conversion.

The brightness adjuster 81 adjusts or corrects the pixel values of the second RGB image signals based on the first RGB image signals and the second RGB image signals. A reason for adjusting the pixel values of the second RGB image signals by the brightness adjuster 81 is as follows. The brightness of the second RGB image signals, which have been subjected to the process for changing color regions (color areas) performed by the angle adjuster 74 and the radial-coordinate adjuster 75, may become significantly different from the brightness of the first RGB image signals. The brightness adjuster 81 adjusts the pixel values of the second RGB image signals to make the brightness of the second RGB image signals after the brightness adjustment equal to the brightness of the first RGB image signals.

The brightness adjuster 81 comprises a first brightness information calculator 81a and a second brightness information calculator 81b. The first brightness information calculator 81a calculates first brightness information Yin based on the first RGB image signals. The second brightness information calculator 81b calculates second brightness information Yout based on the second RGB image signals. The first brightness information calculator 81a calculates the first brightness information Yin with the use of an arithmetic expression "kr×pixel value of first R image signal+kg×pixel value of first G image signal+kb×pixel value of first B image signal". The second brightness information calculator 81b calculates the second brightness information Yout in a manner similar to that of the first brightness information calculator 81a, with the use of an arithmetic expression similar to that described above. After calculating the first brightness information Yin and the second brightness information Yout, the brightness adjuster 81 performs arithmetic operations based on the expressions (E1) to (E3), thereby adjusting the pixel values of the second RGB image signals.

$$R^* = \text{pixel value of second } R \text{ image signal} \times Yin/Yout \qquad (E1)$$

$$G^* = \text{pixel value of second } G \text{ image signal} \times Yin/Yout \qquad (E2)$$

$$B^* = \text{pixel value of second } B \text{ image signal} \times Yin/Yout \qquad (E3)$$

Note that "$R^*$" denotes the second R image signal after the brightness adjustment. "$G^*$" denotes the second G image signal after the brightness adjustment. "$B^*$" denotes the second B image signal after the brightness adjustment. Each of "kr", "kg", and "kb" is any constant within a range from 0 to 1.

The color tone converter 82 (corresponding to the pseudo-color display processor of the present invention) performs a color tone converting process for converting the second R image signal, the second G image signal and the second B image signal into the red display signal, the green display signal, and the blue display signal by the matrix processing (M1) (corresponding to the first color tone converting process of the present invention) based on following Formula 1.

[Formula 1]

$$\begin{pmatrix} Rd \\ Gd \\ Bd \end{pmatrix} = \begin{pmatrix} 0 & k1 & 0 \\ 0 & 0 & k2 \\ 0 & 0 & k3 \end{pmatrix} * \begin{pmatrix} R^* \\ G^* \\ B^* \end{pmatrix} \qquad (M1)$$

In Formula 1, "Rd" represents the red display signal, "Gd" represents the green display signal, and "Bd" represents the blue display signal. Each of "k1", "k2", and "k3" is any constant within a range from 0 to 1. The red display signal (Rd) is the signal corresponding to the R channel of the monitor 18, and obtained by multiplying the second G image signal by the coefficient k1, as shown in the matrix processing M1. The green display signal (Gd) is the signal corresponding to the G channel of the monitor 18, and obtained by multiplying the second B image signal by the coefficient k2. The blue display signal (Bd) is the signal corresponding to the B channel of the monitor 18, and obtained by multiplying the second B image signal by the coefficient k3. In other words, the red display signal, the green display signal and the blue display signal are obtained only using the second B image signal and the second G image signal, without using the second R image signal.

As described above, in case that the special image is displayed on the monitor 18 based on the three color display signals consisting of the red display signal, the green display signal and the blue display signal, the special image is displayed in pseudo colors in which blood vessels in the special image are displayed with a different color according to each depth (e.g., superficial blood vessels are displayed with a brown tone, and middle-deep blood vessels are displayed with a cyan tone). In addition, by displaying the special image in pseudo colors, color differences among the first color range, the second color range, the third color range, the fourth color range and the fifth color range become clearer.

The structure enhancer 78 performs the structure enhancement process on the red display signal, the green display signal and the blue display signal. Frequency filtering or the like may be used for the structure enhancement process. The inverse log converter 79 performs inverse log conversion on the red display signal, the green display signal and the blue display signal which have passed through the structure enhancer 78. Thereby the red display signal, the green display signal and the blue display signal with antilogarithmic pixel values are obtained. The gamma converter 80 performs the gamma conversion on the red display signal, the green display signal and the blue display signal which have passed through the inverse log converter 79. Thereby the red display signal, the green display signal and the blue display signal with the tone suitable for an output device such as the monitor 18 are obtained. The red display signal, the green display signal and the blue display signal, which have passed through the gamma converter 80, are transmitted to the video signal generator 66.

Figure 5:
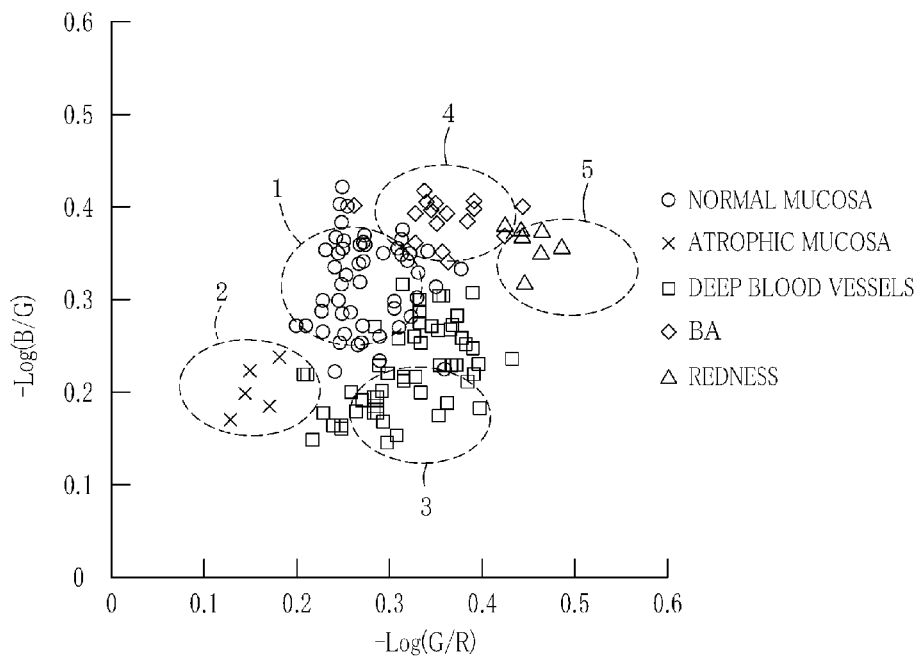
FIG. 5 is a graph illustrating a distribution of a first color range, a second color range, a third color range, a fourth color range and a fifth color range in the signal ratio space.

Hereinafter, a process for adjusting an angle θ, which is performed by the angle adjuster 74, is described. As illustrated in FIG. 5, in the signal ratio space, being the feature space formed by the B/G ratio and the G/R ratio, all of the first color range, the second color range, the third color range, the fourth color range and the fifth color range are distributed in the first quadrant. The first color range mostly contains the B/G ratio and the G/R ratio corresponding to the normal mucosa (In FIG. 5, "○" denotes the normal mucosa), and is located substantially at the center in the first quadrant of the signal ratio space. The second color range mostly contains the B/G ratio and the G/R ratio corresponding to the atrophic mucosa (In FIG. 5, "x" denotes the atrophic mucosa), and is located at the lower left from the first color range. The third area mostly contains the B/G ratio and the G/R ratio corresponding to deep blood vessels (In FIG. 5, "□" denotes the deep blood vessels), and is located at the lower right from the first color range. The fourth area mostly contains the B/G ratio and the G/R ratio corresponding to BA (Brownish Area) (In FIG. 5, "◇" denotes the BA), and is located at the upper right from the first color range. The fifth area mostly contains the B/G ratio and the G/R ratio corresponding to redness (In FIG. 5, "Δ" denotes the redness), and is located at the right from the first color range.

Figure 6:
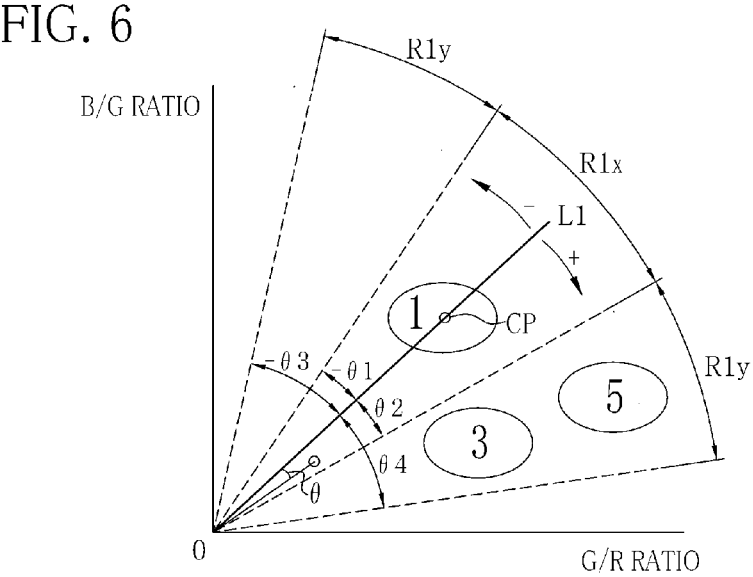
FIG. 6 is an explanatory view illustrating how to adjust an angle θ.

As illustrated in FIG. 6, the angle adjuster 74 sets a first reference line L1 to pass through the barycentric position CP of the first color range in the signal ratio space, to adjust an angle θ. The barycentric position CP of the first color range is calculated from the B/G ratio and the G/R ratio in the first color range, by a predetermined calculation (e.g., the mean value). The first reference line L1 does not necessarily pass through the barycentric position CP of the first color range but at least passes through the first color range.

The angle adjuster 74 performs an equal angular scaling process (angle maintaining process) (for the signal ratio space). In the equal angular scaling process, an angle θ within a predetermined region R1x, which includes the first reference line L1, is maintained unchanged based on the angle change rate W1x. The region R1x is set so include the first color range. Note that an angle θ is defined by an angle from the first reference line L1. The angle θ is defined as a positive angle in the clockwise direction from the first reference line L1 and defined as a negative angle in the counterclockwise direction from the first reference line L1. The region R1x includes the angle θ ranging from "−θ1", which is less than "0", to "+θ2", which is greater than "0".

In a case where the angle θ is within a region R1y, which is located outside the region R1x, the angle adjuster 74 performs an angle adjustment process, in which the angle θ is changed based on an angle change rate W1y that is greater or less than the angle change rate W1x. The region R1y is set to include the third color range and the fifth color range. The region R1y includes a negative angle range from "−θ3", which is less than "−θ1", to "−θ1" and a positive angle range from "+θ2" to "+θ4", which is greater than "+θ2".

Figure 7:
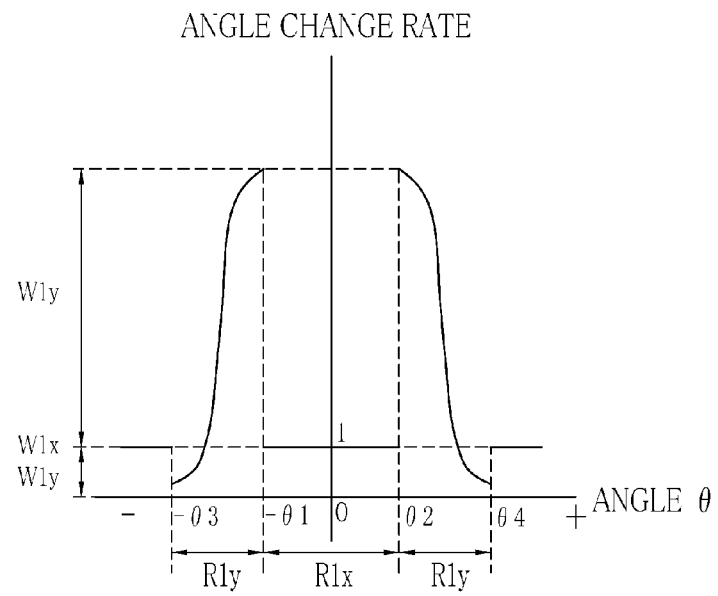
FIG. 7 is a graph illustrating a relationship between an angle θ and an angle change rate.

As illustrated in FIG. 7, the angle change rate W1x for an angle θ within the region R1x, in which the equal angular scaling process is to be performed, is set to 1.0. Thereby the angle θ before the equal angular scaling process is equivalent to the angle θ after the equal angular scaling process in the region R1x. The angle change rate W1y for an angle θ within the region R1y, in which the angle adjustment process is to be performed, is set to greater than or less than 1.0. Thereby the angle θ is changed by the angle adjustment process. In the positive angle range of the region R1y, the angle change rate W1y is the highest and greater than 1.0 in the case where the angle θ is "+θ2" and the angle change rate W1y decreases as the angle θ increases. The angle change rate W1y falls below 1.0 when the angle θ exceeds a predetermined value.

In the negative angle range of the region R1y, the angle change rate W1y is the highest and greater than 1.0 in the case where the angle θ is "−θ1" and the angle change rate W1y decreases as the angle θ decreases. The angle change rate W1y falls below 1.0 when the angle θ falls below a predetermined value. Note that the angle change rate is set to 1.0 in the case where the angle θ is greater than "θ4" or less than "−θ3".

Figure 8:
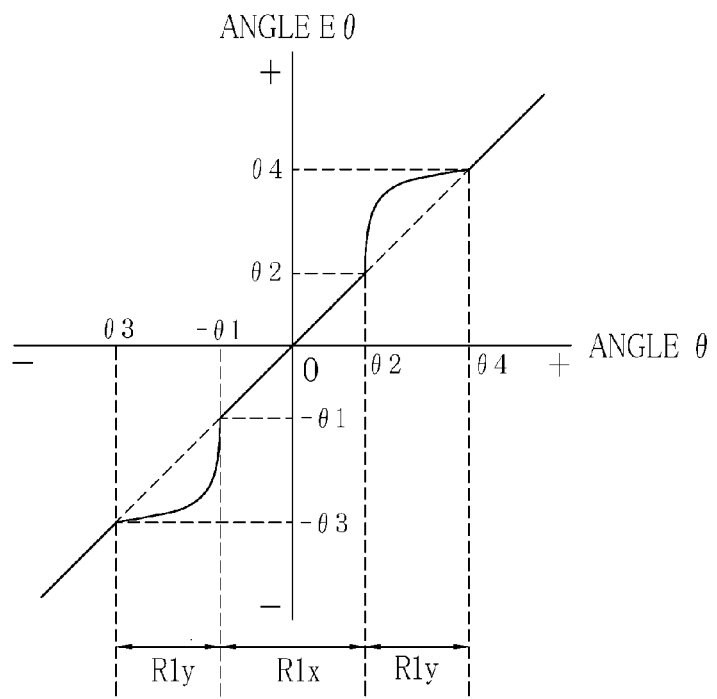
FIG. 8 is a graph illustrating a relationship between angles θ and Eθ.

As illustrated in FIG. 8, the angle θ in the region R1x is changed to the angle Eθ that is equivalent to the angle θ (Eθ=θ) through the equal angular scaling process. Also in the case where the angle θ is greater than "θ4" or less than "−θ3", the angle θ is changed to the angle Eθ that is equivalent to the angle θ (Eθ=θ). In the case where the angle θ is in the positive angle range of the region R1y, the angle θ is changed to the positive angle Eθ that is greater than or equal to the angle θ (Eθ≥θ). In the case where the angle θ is in the negative angle range of the region R1y, the angle θ is changed to the negative angle Eθ that is less than or equal to the angle θ (Eθ≥θ).

The following operation and effect are obtained by changing the angles. As illustrated in a part (A) of FIG. 9, the first color range, the third color range and the fifth color range are close to each other before the equal angular scaling process and the angle adjustment process. As illustrated in a part (B) of FIG. 9, after the equal angular scaling process and the angle adjustment process, the coordinates corresponding to the third color range and the fifth color range are moved in the clockwise direction A1 with respect to the first reference line L1 while the position of the first color range is maintained unchanged in the signal ratio space. Thereby, the differences in hue among the first color range, the third color range and the fifth color range are increased.

As described above, in the special image obtained by enlarging the differences in hue among the first color range, the third color range and the fifth color range, color differences between the normal mucosa and the part including deep blood vessels and between the normal mucosa and the part including redness can be clearly displayed. Note that in FIG. 9, "1" denotes the first color range, "3" denotes the third color range, and "5" denotes the fifth color range. Note that in the part (B) of FIG. 9, the ranges illustrated by solid lines represent the ranges after the equal angular scaling process and the angle adjustment process for the signal ratio space, and the ranges illustrated by dotted lines represent the ranges before the equal angular scaling process and the angle adjustment process (the same for a part (B) of FIG. 13)

Hereinafter, a process for adjusting the radial coordinate r, which is performed by the radial-coordinate adjuster 75, is described. As illustrated in FIG. 10, the radial coordinate adjuster 75 sets the first reference line L1 to pass through the barycentric position CP of the first color range and sets a second reference line L2 to pass through the barycentric position CP of the first color range and cross the first reference line L1 in the signal ratio space, to adjust a radial coordinate r. Note that the second reference line L2 does not necessarily pass through the barycentric position CP of the first color range but at least passes through the first color range.

In a case where a radial coordinate r is in a predetermined region R2x, which includes the second reference line L2, the radial-coordinate adjuster 75 performs an equal radial-coordinate scaling process (a radial-coordinate maintaining process) (for the signal ratio space). In the equal radial-coordinate scaling process, the radial coordinate r is maintained unchanged based on the radial-coordinate change rate W2x. The region R2x is set to include the first color range. The region R2x includes the radial coordinates r ranging from "r1", which is less than "rc", being the radial coordinate corresponding to the second reference line L2, to "r2", which is greater than "rc". In a case where the radial coordinate r is within a region R2y, which is located outside the region R2x, the radial-coordinate adjuster 75 performs a radial-coordinate adjustment process, in which the radial coordinate r is changed based on a radial-coordinate change rate W2y that is greater or less than the radial-coordinate change rate W2x. The region R2y includes a small radial-coordinate range and a large radial-coordinate range. The small-coordinate range is from "r3", which is less than "r1", to "r1". The large radial-coordinate range is from "r2" to "r4", which is greater than "r2".

As illustrated in FIG. 11, in the case where the radial coordinate r is in the region R2x, in which the equal radial-coordinate scaling process for the signal ratio space is to be performed, the radial-coordinate change rate W2x is set to 1.0. Thereby the radial coordinate r before the equal radial-coordinate scaling process is equivalent to the radial coordinate r after the equal radial-coordinate scaling process in the region R2x. The radial-coordinate change rate W2y for a radial-coordinate r within the region R2y, in which the radial-coordinate adjustment process is to be performed, is set to greater than or less than 1.0. Thereby the radial-coordinate r is changed by the radial-coordinate adjustment process. In the small radial-coordinate range of the region R2y, the radial-coordinate change rate W2y is the highest and greater than 1.0 in the case where the radial-coordinate r is "r1" and the radial-coordinate change rate W2y decreases as the radial-coordinate r decreases. The radial-coordinate change rate W2y falls below 1.0 when the radial-coordinate r falls below a predetermined value.

In the large radial-coordinate range of the region R2y, the radial-coordinate change rate W2y is the highest and greater than 1.0 in the case where the radial-coordinate r is "r2" and the radial-coordinate change rate W2y decreases as the radial-coordinate r increases. The radial-coordinate change rate W2y falls below 1.0 when the radial-coordinate r exceeds a predetermined value. Note that the radial-coordinate change rate is set to 1.0 in the case where the radial-coordinate r is greater than "r4" or less than "r3".

As illustrated in FIG. 12, the radial coordinate r in the region R2x is changed to the radial coordinate Er that is equivalent to the radial coordinate r (Er=r) through the equal radial-coordinate scaling process for the signal ratio space. Also in the case where the radial coordinate r is greater than "r4" or less than "r3", the radial coordinate r is changed to the radial coordinate Er that is equivalent to the radial coordinate r (Er=r). In the case where the radial coordinate r is in the small radial-coordinate range of the region R2y, the radial coordinate r is changed to the radial coordinate Er that is less than or equal to the radial coordinate r (Er≥r) through the radial-coordinate adjustment process. In the case where the radial coordinate r is in the large radial-coordinate range of the region R2y, the radial coordinate r is changed to the radial coordinate Er that is greater than or equal to the radial coordinate r (Er≥r) through the radial-coordinate adjustment process.

The following operation and effect are obtained by changing the radial coordinates. As illustrated in a part (A) of FIG. 13, before the equal radial-coordinate magnification process and the radial-coordinate adjustment process, the first color range, the second color range and the fourth color range are close to each other. As illustrated in a part (B) of FIG. 13, after the equal radial-coordinate magnification process and the radial-coordinate adjustment process, most of the coordinates corresponding to the fourth color range are moved away from the origin "0" in a direction A2 while the position of the first color range is maintained unchanged in the signal ratio space. On the other hand, most of the coordinates corresponding to the second color range are moved toward the origin "0" in a direction A3. Thereby, the differences in saturation among the first color range, the second color range and the fourth color range are increased.

As described above, in the special image with enlarged the differences in saturation among the first color range, the second color range and the fourth color range, color differences between the normal mucosa and the atrophic mucosa and between the normal mucosa and the part including redness can be clearly displayed. Note that in FIG. 13, "1" denotes the first color range, "2" denotes the second color range, and "4" denotes the fourth color range.

Next, referring to a flowchart in FIG. 14, a procedure of the observation of the object in the special mode is described. First, the observation mode is set to the normal mode. The insertion section 12a of the endoscope 12 is inserted into the body cavity. After the distal end portion 12d of the insertion section 12a reaches the stomach, the mode SW 13 is operated to switch from the normal mode to the special mode.

Upon switching to the special mode, the source controller 21 performs the specific light quantity control to make the quantities of the violet light V and the green light G larger than the quantity of the red light R. The RGB image signals are obtained by capturing the object illuminated with the violet light V, the blue light B, the green light G and the red light R under the specific light quantity control. The signal ratio calculator 72 calculates the B/G ratio and the G/R ratio based on the obtained first RGB image signals. Then, the B/G ratio and the G/R ratio are converted into the radial coordinate r and the angle θ through the polar coordinate conversion.

Next, the angle adjuster 74 performs the equal angular scaling process and the angle adjustment process. In the equal angular scaling process, an angle in the region R1x, which includes the first reference line L1 passing through the barycentric position CP of the first color range, is maintained unchanged. An angle in the region R1y, which is located outside the region R1X, is expanded or compressed through the angle adjustment process. As a result of the equal angular scaling process and the angle adjustment process, the third color range and the fifth color range move along a clock-wise direction A1 (refer to FIG. 9), while the position of the second area is maintained unchanged in the signal ratio space. Thereby the differences in hue among the first color range, the third color range and the fifth color range are increased.

After the angle adjustment is finished, the radial-coordinate adjuster 75 performs the equal radial-coordinate scaling process of the region R2x and the radial-coordinate adjustment process of the region R2y. The region R2x includes the second reference line L2, which passes through the barycentric position CP of the first color range and intersects the first reference line L1. The region R2y is located outside the region R2x. As a result of the equal radial-coordinate scaling process and the radial-coordinate adjustment process, the fourth color range is moved away from the origin "0" in the direction A2 and the second color range is moved toward the origin "0" in the direction A3, while the position of the first color range is maintained unchanged in the signal ratio space (refer to FIG. 13).

Then, the RGB signal converter 77 converts the B/G ratio and the G/R ratio after the angular adjustment and the radial coordinate adjustment, into the second RGB image signals. The second G image signal is converted into the red display signal, the second B image signal is converted into the green display signal, and the second B image signal is converted into the blue display signal. Based on these three color display signals, the special image is displayed. In this special image, the angular adjustment and the radial coordinate adjustment on the signal ratio space make the color difference between the first color range and the second color range, the third color range, the fourth color range, and the fifth color range clear. In addition, since the special image is displayed in pseudo colors, visibility of the blood vessels varying in depth improves.

Furthermore, due to the specific light quantity control to make the quantities of the violet light V and the green light G larger than the quantity of the red light R, the sensibility of the second B image signal and the second G image signal become higher than the sensitivity of the second R image signal. Accordingly, in the special image, the color difference between the first color range and other color ranges such as the second color range becomes further clearer, and the vascular visibility further improves, in comparison with the case that the specific light quantity control is not performed.

In addition, for conversion to the three color display signals used for display of the special image, only the second G image signal and the second B image signal are used but the second R image signal is not used among the second RGB image signals after subjected to the angular adjustment and the radial coordinate adjustment. Therefore, actually in the angular adjustment and the radial coordinate adjustment, the second color range, the third color range and the fifth color range are moved along the negative direction of the vertical axis (the B/G ratio) but not along the horizontal axis (the G/R ratio) in the signal ratio space. In addition, the fourth color range is moved along the positive direction of the vertical axis but not along the horizontal axis (refer to FIG. 15).

Note that in the above embodiment 1A, as shown in the matrix processing (M1), without using the second R image signal, only the second B image signal and the second G image signal are converted to the three color display signals. However, the second R image signal may be used in addition to the second B image signal and the second G image signal to be converted to the three color display signals. In this case, the second RGB image signals are converted into the red display signal, the green display signal, and the blue display signal by the matrix processing (M2) (corresponding to the second color tone converting process of the present invention) based on following Formula 2.

[Formula 2]

$$\begin{pmatrix} Rd \\ Gd \\ Bd \end{pmatrix} = \begin{pmatrix} p1 & k1 & 0 \\ p2 & 0 & k2 \\ p3 & 0 & k3 \end{pmatrix} * \begin{pmatrix} R^* \\ G^* \\ B^* \end{pmatrix} \quad (M2)$$

In Formula 2, "R*", "G*", "B*", "Rd", "Gd", "Bd", "k1", "k2" and "k3" are the same as in Formula 1. Each of "p1", "p2", and "p3" is any constant within a range from 0 to 1, and in the relation of "p1=p2=p3" or p1≈p2≤p3". In addition, "p1", "p2", "p3" are set extremely small with compared to "k1", "k2", "k3".

As shown in the above matrix processing M2, the red display signal (Rd) is obtained by the first weighting operation, in which the second R image signal is multiplied by the coefficient p1, and the second G image signal is multiplied by the coefficient k1 extremely larger than the coefficient p1. The green display signal (Gd) is obtained by the second weighting operation, in which the second R image signal is multiplied by the coefficient p2, and the second B image signal is multiplied by the coefficient k2 extremely larger than the coefficient p2. The blue display signal (Bd) is obtained by the third weighting operation, in which the second R image signal is multiplied by the coefficient p3, and the second B image signal is multiplied by the coefficient k3 extremely larger than the coefficient p3. It is preferable that the coefficient k1 is larger than 10 times of the coefficient p1, the coefficient k2 is larger than 10 times of the coefficient p2, and the coefficient k3 is larger than 10 times of the coefficient p3.

In the special image based on the red display signal, the green display signal and the blue display signal obtained by the matrix processing M2, information that only the second R image signal has can be displayed, since the signal value of the second R image signal is added though it is little, in addition to emphasize the color differences between the first color range and other color ranges such as the second color range and display them in pseudo colors. For example, since the second R image signal contains many of contents of the red light V which has a high reflectance on the object, a lot of information about irregularity information of the object including the thickening is included in the second R image signal. In addition, the coefficients p1, p2 and p3 for the weighting of the second R image signal are extremely smaller than the coefficient k1 for the weighting of the second G image signal and the coefficients k2 and k3 for the weighting of the second B image signal, and those three coefficients are equal or about the same. Therefore, the special image obtained based on the matrix processing M2 is nearly unchanged from the special image obtained based on the matrix processing M1, in tones of the pseudo colors.

Note that in the above embodiment 1A, the sensibility of the second B image signal and the second G image signal become higher than the sensitivity of the second R image signal by the specific light quantity control to make the quantities of the violet light V and the green light G larger than the quantity of the red light R. However, instead of or adding to this control, the image controller 49 may perform a specific imaging control so that the sensibility of the B pixel and the G pixel become higher than the sensitivity of the R pixel. In addition, by the specific light quantity control, instead of or adding to the violet light V, the quantity of the blue light B may be made larger than the quantity of the red light R.

As an example of the specific imaging control, FIG. 16 illustrates that a charge accumulation time Tb of the B pixel and a charge accumulation time Tg of the G pixel are made longer than a charge accumulation time Tr of the R pixel, in a period of one frame indicating the period necessary to generate one frame of the special image. Accordingly, the sensitivities of the B pixel and the G pixel can be made higher than the sensitivity of the R pixel. To control each charge accumulation time to be different between the B pixel and the G pixel and the R pixel, it is required that each pf the B pixel, the G pixel and the R pixel in the image sensor 48 can independently perform reading operation of the image signal. In FIG. 16, the charge accumulation time Tb of the B pixel is made longer than the charge accumulation time Tg of the G pixel. However, the charge accumulation time Tb of the B pixel may be made shorter than the charge accumulation time Tg of the G pixel, or the charge accumulation time Tb of the B pixel may be made equal to the charge accumulation time Tg of the G pixel.

Embodiment 1B

In the above embodiment 1A, the signal ratio calculator 72 calculates the B/G ratio and the G/R ratio from the first RGB image signals. In the feature space formed by the B/G ratio and the G/R ratio, the equal angular scaling process, the angle adjustment process, the equal radial-coordinate scaling process and the radial-coordinate adjustment process are performed. In an embodiment 1B, chrominance signals Cr and Cb are obtained as the color information. In a feature space formed by the chrominance signals Cr and Cb, the equal angular scaling process, the angle adjustment process, the equal radial-coordinate scaling process and the radial-coordinate adjustment process are performed.

In the embodiment 1B, a special image processor 92 (refer to FIG. 17) is used. Unlike the special image processor 64, the special image processor 92 is not provided with the log converter 71, the signal ratio calculator 72, and the inverse log converter 79. Instead, the special image processor 92 comprises a luminance/chrominance signal converter 85 between the inverse gamma converter 70 and the polar coordinate converter 73. The components, other than those described above, of the special image processor 92 are the same as or similar to the components of the special image processor 64.

The luminance/chrominance signal converter 85 (which corresponds to the color information obtaining processor of the present invention) converts the first RGB image signals into a luminance signal Y and the chrominance signals Cr and Cb. A well-known conversion equation is used for the conversion into the chrominance signals Cr and Cb. The chrominance signals Cr and Cb are transmitted to the polar coordinate converter 73. The luminance signal Y is transmitted to the RGB converter 77 and the brightness adjuster 81. The RGB converter 77 converts the chrominance signals Cr and Cb, which passed through the Cartesian coordinate converter 76, and the luminance signal Y into the second RGB image signals. The brightness adjuster 81 adjusts the pixel values of the second RGB image signals with the use of the luminance signal Y (the first brightness information Yin) and the second brightness information (the second brightness information Yout), which is calculated by the second brightness information calculator 81*b*. Note that the method for calculating the second brightness information Yout and the method for adjusting the pixel values of the second RGB image signals are the same as or similar to those of the special image processor 64.

In a feature space (hereinafter referred to as the Cb-Cr space) formed by the chrominance signal Cr (the vertical axis) and the chrominance signal Cb (the horizontal axis), the special image processor 92 performs the equal angular scaling process, the angle adjustment process, the equal radial-coordinate scaling process and the radial-coordinate adjustment process (for the Cb-Cr space). In the Cb-Cr space, as illustrated in FIG. 18, all of the first color range, the second color range, the third color range, the fourth color range and the fifth color range are located in the second quadrant of the Cb-Cr space. The first color range is located substantially at the center in the second quadrant, the second color range is located at the lower right from the first color range, the third color range is located at the lower from the first color range, the fourth color range is located at the upper left from the first color range, and the fifth color range is located at the left from the first color range.

The equal angular scaling process and the angle adjustment process (for the Cb-Cr space), which are performed by the angle adjuster 74, are substantially similar to the equal angular scaling process and the angle adjustment process (for the signal ratio space), respectively. An angle in the region R1*x*, which includes the first reference line L1 passing through the first color range, is maintained unchanged. An angle in the region R1*y*, which is located outside the region R1*x*, is expanded or compressed. Accordingly, the third color range and the fifth color range move along a counter-clockwise direction A4 (refer to FIG. 19), while the position of the first color range is maintained unchanged in the Cb-Cr space. Thereby the differences in hue among the first color range, the third color range and the fifth color range are increased. In FIG. 19, note that the areas depicted with dotted lines are those before the angle adjustment process (for the Cb-Cr space). The areas depicted with solid lines are those after the angle adjustment process (for the Cb-Cr space). The same applies to FIG. 20.

An equal radial-coordinate scaling process and the radial-coordinate adjustment process (for the Cb-Cr space), which are performed by the radial-coordinate adjuster 75, are substantially similar to the equal radial-coordinate scaling process and the radial-coordinate adjustment process (for the signal ratio space). In the equal radial-coordinate scaling process, a radial coordinate in the region R1*x*, which includes the second reference line L2 passing through the first color range and intersecting the first reference line L1, is maintained unchanged. A radial coordinate in the region R1*y*, which is located outside the region R1*x*, is expanded or compressed. As a result, the fourth color range is moved away from the origin "0" in the direction A2 and the second color range is moved toward the origin "0" in the direction A3, while the position of the first color range is maintained unchanged in the Cb-Cr space (refer to FIG. 20). Thus, the differences in hue and saturation among the first color range, the second color range and the fourth color range are increased.

Embodiment 1C

In an embodiment 1C, a lab converter (which corresponds to the color information obtaining processor of the present invention, for example) performs lab conversion of the first RGB image signals to obtain a* and b* (that is, the color components a* and b*, being the color information, of CIE lab space, and the same applies to the following). In a feature space (ab space) formed by a* and b*, the equal angular scaling process, the angle adjustment process, the equal radial-coordinate scaling process and the radial-coordinate adjustment process are performed. Note that CIE Lab refers to a color system defined by CIE (Commission internationale de l'Eclairage or International Commission on Illumination). In addition, the special image processor of the embodiment 1C is approximately similar to the special image processor 64 except that a Lab converter is provided instead of the signal ratio calculator 72 in the special image processor 64 of the embodiment 1A.

In the embodiment 1C, as illustrated in a part (A) of FIG. 21, the first color range, the third color range, and the fifth color range are distributed in the first quadrant of the ab space, as same as in case of the signal ratio space. As a result of an equal angular scaling process and an angle adjustment process (for the ab space), the third color range and the fifth color range move along the clock-wise direction A1 with respect to the first reference line L1 (refer to a (B) part of FIG. 21), while the position of the first color range is maintained unchanged in the ab space. In the (B) part of FIG. 21, note that the areas depicted with dotted lines are those before the angle adjustment process (for the ab space). The areas depicted with solid lines are those after the angle adjustment process (for the ab space). The same applies to a part (B) of FIG. 22.

As illustrated in a part (A) of FIG. 22, the first color range, the second color range, and the fourth color range are distributed in the first quadrant of the ab space, as same as in case of the signal ratio space. As a result of an equal radial-coordinate scaling process and a radial-coordinate adjustment process (for the ab space), the fourth color range is moved away from the origin "0" in the direction A2 and the second color range is moved toward the origin "0" in the direction A3 with respect to the second reference line L2, while the position of the first color range is maintained unchanged in the signal ratio space (refer to the part (B) of FIG. 13). Note that it is preferable that the brightness adjuster 81 adjusts the pixel values of the second RGB image signals obtained after the equal radial-coordinate scaling process and the radial-coordinate adjustment process (for the ab space).

Embodiment 1D

In an embodiment 1D, hue and saturation are obtained as the color information, and the equal angular scaling process, the angle adjustment process, the equal radial-coordinate scaling process and the radial-coordinate adjustment process are executed in a feature space formed from hue and saturation. In the embodiment 1D, a special image processor 96 illustrated in FIG. 23 is used. Unlike the special image processor 64, the special image processor 96 is not provided with the inverse gamma converter 70, the log converter 71, the signal ratio calculator 72, the polar coordinate converter 73, the angle adjuster 74, the radial coordinate adjuster 75, the inverse log converter 79 and the gamma converter 80. Instead, the special image processor 96 is provided with an HSV converter 87, a first parallel shifter 90 and the second parallel shifter 91. Regarding other components, the special image processor 96 is similar to the special image processor 64.

The HSV converter 87 (which corresponds to the color information obtaining processor of the present invention, for example) converts the first RGB signals into hue (H), saturation (S) and value (V). A known transformation is used for conversion to hue (H), saturation (S) and value (V). Hue (H) and saturation (S) are sent to the first parallel shifter 90 and the second parallel shifter 91, and value (V) is sent to the RGB signal converter 77. Details about the first parallel shifter 90 and the second parallel shifter 91 will be described later.

The RGB signal converter 77 converts hue (H) and saturation (S) from the second parallel shifter 91 and value (V) from the HSV converter 87 into the second RGB image signals. The brightness adjuster 81 adjusts the pixel values of the second RGB image signals with use of the first brightness information Yin calculated by the first brightness information calculator 81a and the second brightness information Yout calculated by the second brightness information calculator 81b. Note that the method for calculating the first brightness information Yin and the second brightness information Yout, and the method for adjusting the pixel values of the second RGB image signals are the same as or similar to those of the special image processor 64.

Next, processing by the first parallel shifter 90 and second parallel shifter 91 will be explained using an HS space which is the feature space formed by H (hue) and S (saturation). As illustrated in FIG. 24, in the HS space, the first color range is located substantially at the center, the second color range is located at the left from the first color range, the third color range is located at the lower left from the first color range, the fourth color range is located at the right from the first color range, and the fifth color range is located at the lower right from the first color range.

As illustrated in FIG. 25, the first parallel shifter 90 shifts a range having hue H equal to or less than a predetermined value H1 downward in a parallel direction with a specific amount. The predetermined value H1 is set to a value less than the lower limit of hue H in the first color range. Through the parallel shift process by the first parallel shifter 90, the third color range and the fifth color range are shifted downward in the parallel direction while the position of the first color range is maintained unchanged in the HS space. Thereby the differences in hue between the first color range and the third color range, and between the first color range and the fifth color range are increased. In FIG. 25, note that the areas depicted with dotted lines are those before the parallel shift process by the first parallel shifter 90. The areas depicted with solid lines are those after the parallel shift process by the first parallel shifter 90. The same applies to FIG. 26.

As illustrated in FIG. 26, the second parallel shifter 91 shifts a range having saturation S equal to or less than a predetermined value S1 to the left in a parallel direction with a specific amount, and shifts a range having saturation S equal to or more than a predetermined value S2 to the right in the parallel direction with a specific amount. The predetermined value S1 is set to a value less than the lower limit of saturation S in the first color range, and the predetermined value S2 is set to a value more than the upper limit of saturation S in the first color range. Through the parallel shift process by the second parallel shifter 91, the second color range is shifted to the left and the fourth color range is shifted to the right in the parallel direction while the position of the first color range is maintained unchanged in the HS space. Thereby the differences in saturation between the first color range and the second color range, and between the first color range and the fourth color range are increased.

Embodiment 2

In an embodiment 2, a laser and a phosphor are used, instead of the LEDs 20a to 20d of the four colors described in the embodiments 1A to 1D, to illuminate the object. Other than those, the configuration is the same as or similar to that of the embodiments 1A to 1D.

As illustrated in FIG. 27, in the light source device 14 of an endoscope system 100 according to the embodiment 2, a blue laser source (denoted as 445LD in FIG. 27) 104 and a blue-violet laser source (denoted as 405LD in FIG. 27) 106 are provided in place of the LEDs 20a to 20d of the four colors. The blue laser 104 emits blue laser beams with the center wavelength 445±10 nm. The blue-violet laser 106 emits blue-violet laser beams with the center wavelength 405±10 nm. The light emissions from the semiconductor light emitting elements of the lasers 104 and 106 are controlled individually by a source controller 108. The light quantity ratio between the light (laser beams) from the blue laser 104 and the light (laser beams) from the blue-violet laser 106 is changed as desired.

In the normal mode, the source controller 108 actuates the blue laser 104. In the special mode, the source controller 108 actuates both the blue laser 104 and the blue-violet laser 106 such that the light-emission ratio of the blue laser beams is greater than that of the blue-violet laser beams. The laser beams emitted from each of the lasers 104 and 106 are incident on the light guide (LG) 41 through optical members (e.g. a condenser lens, an optical fiber, a combiner, and the like, all not shown).

Note that the full width at half maximum of the blue laser beams or the blue-violet laser beams is preferred to be in the order of ±10 nm. Broad-area type InGaN-based laser diodes may be used for the blue laser 104 and blue-violet laser 106. The InGaNAs-based laser diodes and the GaNAs-based laser diodes may be used instead or in addition. A light emitting element such as a light emitting diode may be used as the light source.

The illumination optical system 30a is provided with the light lens 45 and a phosphor 110 on which the blue laser beams or the blue-violet laser beams from the light guide 41 are incident. The blue laser beams causes the phosphor 110 to emit fluorescence. A part of the blue laser beams passes through the phosphor 110. The blue-violet laser beams pass through the phosphor 110 without exciting the phosphor. The light from the phosphor 110 is applied to the object through the light lens 45.

In the normal mode, the blue laser beams are mostly incident on the phosphor 110, so that the white light, being the combination of the blue laser beams and the fluorescence from the phosphor 110 excited by the blue laser beams, is applied to the object as illustrated in FIG. 28. In the special mode, both the blue-violet laser beams and the blue laser beams are incident on the phosphor 110, so that the special light, being the combination of the blue-violet laser beams, the blue laser beams, and the fluorescence from the phosphor 110 excited by the blue laser beams, is applied to the object as illustrated in FIG. 29.

Note that it is preferred to use the phosphor 110 containing two or more types of phosphor components (e.g. YAG-based phosphor, BAM ($BaMgAl_{10}O_{17}$), or the like) that absorb a part of the blue laser beams and emit light of green to yellow. In the case where the semiconductor light emitting elements are used as the excitation light sources for the phosphor 110 as described in this example, the high-intensity white light is provided with high light-emission efficiency, the intensity of the white light is controlled easily, and the variations in the color temperature and chromaticity of the white light are small.

Embodiment 3

In an embodiment 3, instead of the LEDs 20a to 20d of the four colors described in the embodiments 1A to 1D, a broadband light source (e.g. a xenon lamp) and a rotary filter are used to illuminate the object. Instead of the color image sensor 48, a monochrome image sensor is used to capture the images of the object. The components other than those are the same as or similar to the components described in the embodiments 1A to 1D.

As illustrated in FIG. 30, in an endoscope system 200 of the embodiment 3, a broadband light source 202, a rotary filter 204, and a filter switcher 205 are provided instead of the LEDs 20a to 20d in the light source device 14. The imaging optical system 30b is provided with a monochrome image sensor 206 with no color filter, in place of the color image sensor 48.

The broadband light source 202 is composed of a xenon lamp, a white LED, or the like, and emits the white light in the wavelength range from blue to red. The rotary filter 204 comprises a normal filter 208 provided on the inner side and a special filter 209 provided on the outer side (see FIG. 31). The normal filter 208 is used in the normal mode. The special filter 209 is used in the special mode. The filter switcher 205 shifts the rotary filter 204 in the radial direction. In a case where the observation mode is set to the normal mode by the operation of the mode SW 13, the filter switcher 205 inserts the normal filter 208 of the rotary filter 204 into the light path of the white light. In a case where the observation mode is set to the special mode, the filter switcher 205 inserts the special filter 209 of the rotary filter 204 into the light path of the white light.

As illustrated in FIG. 31, the normal filter 208 comprises a B filter 208a, a G filter 208b, and an R filter 208c in a circumferential direction. The B filter 208a transmits the blue light of the white light. The G filter 208b transmits the green light of the white light. The R filter 208c transmits the red light of the white light. In the normal mode, the blue light, the green light, and the red light are alternately applied to the object as the rotary filter 204 is rotated.

The special filter 209 comprises a Bn filter 209a, a G filter 209b, and an R filter 209c in the circumferential direction. The Bn filter 209a transmits blue narrowband light in a specific wavelength range of the white light. The G filter 209b transmits the green light of the white light. The R filter 209c transmits the red light of the white light. In the special mode, the blue narrowband light, the green light, and the red light are alternately applied to the object as the rotary filter 204 is rotated.

In the endoscope system 200, in the normal mode, the monochrome image sensor 206 captures an image of the object every time the blue light, the green light, or the red light is applied to the object. Thereby, the three colors (RGB) of image signals are obtained. The normal image is produced based on the RGB image signals in a manner the same as or similar to those in the embodiments 1A to 1D.

In the special mode, the image sensor 206 captures an image of the object every time the blue narrowband light, the green light, or the red light is applied to the object. Thereby, the Bn image signal, the G image signal, and the R image signal are obtained. The special image is produced based on the Bn image signal, the G image signal, and the R image signal. The Bn image signal is used in place of the B image signal to produce the special image. Other than that, the special image is produced in a manner the same as or similar to those of the embodiments 1A to 1D.

Embodiment 4

In an embodiment 4, a capsule endoscope, which is to be swallowed by a patient, is used in place of the insertion-type endoscope 12 and the light source device 14. The RGB image signals necessary for producing a normal image or a special image are obtained from the capsule endoscope.

As illustrated in FIG. 32, a capsule endoscope system 300 according to the embodiment 4 comprises a capsule endoscope 302, a transmission/reception antenna 304, a receiving device 306 for the capsule endoscope 302, the processor device 16, and the monitor 18. The capsule endoscope 302 comprises an LED 302a, an image sensor 302b, an image processor 302c, and a transmission antenna 302d. Note that the processor device 16 is the same as or similar to the ones used in the embodiments 1A to 1D. In the embodiment 4, a mode switch (SW) 308 is provided to switch between the normal mode and the special mode.

Inside the capsule endoscope 302, two or more LEDs 302a that emit white light are provided. It is preferred that the LED 302a is a white light LED which comprises a blue light source and a phosphor which converts wavelengths of light from the blue light source into fluorescence. An LD (laser diode) may be used instead of the LED. The object is illuminated with the white light from the LED 302a.

The image sensor 302b is a color image sensor. The image sensor 302b captures an image of the object illuminated with the white light and outputs the RGB image signals. It is preferred that the image sensor 302b is a CCD (Charge Coupled Device) image sensor or a CMOS (Complementary Metal-Oxide Semiconductor) image sensor. The image processor 302c performs a process to convert the RGB image signals, which are outputted from the image sensor 302b, into signals to be transmitted through the transmission antenna 302d. The RGB image signals, which have passed through the image processor 302c, are transmitted wirelessly from the transmission antenna 302d to the transmission/reception antenna 304.

The transmission/reception antenna 304 is affixed to the subject's body, and receives the RGB image signals from the transmission antenna 302d. The transmission/reception antenna 304 wirelessly transmits the received RGB image signals to the receiving device 306. The receiving device 306 is connected to the input processor 53 of the processor device 16, and transmits the RGB image signals from the transmission/reception antenna 304 to the input processor 53.

Note that, in the above embodiments, the four colors of light with the emission spectra illustrated in FIG. 3 are used by way of example. However, the emission spectra are not limited to this example. For example, as illustrated in FIG. 33, the green light G and the red light R may have the same spectra as those illustrated in FIG. 3. The violet light Vp may have the center wavelength 410 to 420 nm in a wavelength range slightly shifted to a longer wavelength side than that of the violet light V in FIG. 3. The blue light Bp may have the center wavelength 445 to 460 nm in a wavelength range slightly shifted to a shorter wavelength side than that of the blue light B in FIG. 3.

Note that, in the embodiment 1A, the B/G ratio and the G/R ratio are converted into the radial coordinate r and the angle θ through the polar coordinate conversion. Then the equal angular scaling process, the angle adjustment process, the equal radial-coordinate scaling process and the radial-coordinate adjustment process are performed. Thereafter, the radial coordinate r and the angle θ are converted back into the B/G ratio and the G/R ratio. Alternatively, as illustrated in FIG. 34, a two-dimensional LUT 400 may be used to directly convert the B/G and G/R ratios into the processed B/G and G/R ratios, which have been subjected to the equal angular scaling process, the angle adjustment process, the equal radial-coordinate scaling process and the radial-coordinate adjustment process, without the polar coordinate conversion.

Note that the two-dimensional LUT 400 stores the B/G and G/R ratios in association with the processed B/G and G/R ratios, which have been subjected to the equal angular scaling process, the angle adjustment process, the equal radial-coordinate scaling process and the radial-coordinate adjustment process, which are performed based on the B/G and G/R ratios. The first RGB image signals outputted from the inverse gamma converter 70 are inputted to the two-dimensional LUT 400 and the RGB signal converter 77.

In addition, regarding the chrominance signals illustrated in the embodiment 1B, the color components a* and b* of the color information of Lab illustrated in the embodiment 1C, and H (hue) and S (saturation) illustrated in the embodiment 1D, a two-dimensional LUT may be used to directly convert them into the processed chrominance signals or so on, which have been subjected to the equal angular scaling process, the angle adjustment process, the equal radial-coordinate scaling process and the radial-coordinate adjustment process, without the polar coordinate conversion.

In the above embodiment, the equal radial-coordinate scaling process and the radial-coordinate adjustment process are performed after the equal angular scaling process and the angle adjustment process. Note that the equal radial-coordinate scaling process and the radial-coordinate adjustment process may be performed prior to the equal angular scaling process and the angle adjustment process.

Note that the present invention is applicable to various types of medical image processing devices in addition to the processor devices incorporated the endoscope systems described in the embodiments 1 to 3 and the capsule endoscope system described in the embodiment 4.

Note that each component related to the image processing in the processor device 16 and the imaging control of the endoscope 12 of the present invention is composed by one or more CPUs (Central Processing Units), and is activated by loading programs to the CPU, the programs being stored in a memory (not illustrated) provided in each of the processor device 16 and the endoscope 12. Various changes and modifications are possible in the present invention and may be understood to be within the present invention.

What is claimed is:

1. A medical image processing device comprising:
   an input processor configured to perform an input process of a first red signal, a first green signal and a first blue signal obtained by capturing a reflection image of an object in a body cavity;
   a color information obtaining processor configured to obtain first color information from the first red signal, the first green signal and the first blue signal, the first color information being included in one of color ranges in a feature space formed by the first color information, according to a condition of the object;
   an expansion processor configured to obtain second color information by a selective expansion processing in which color ranges except a first color range are moved in the feature space to expand a distance between the first color range and the other color ranges in the feature space, the first color range corresponding to a normal part in the object, and the other color ranges corresponding to different abnormal parts in the object;
   an RGB signal converter configured to convert the second color information to a second red signal, a second green signal and a second blue signal; and
   a pseudo-color display processor configured to obtain a red display signal, a green display signal and a blue display signal for displaying a medical image, by applying a pseudo-color display process to the second red signal, the second green signal and the second blue signal.

2. The image processing device according to claim 1, wherein the pseudo-color display process is a first color tone converting process to convert the second blue signal to the blue display signal and the green display signal and convert the second green signal to the red display signal.

3. The image processing device according to claim 1, wherein the pseudo-color display process is a second color tone converting process to obtain the blue display signal by applying a first weighting operation to the second blue signal and the second red signal, obtain the green display signal by applying a second weighting operation to the second blue signal and the second red signal, and obtain the red display signal by applying a third weighting operation to the second green signal and the second red signal.

4. The image processing device according to claim 1, wherein the expansion processor includes an angle adjuster configured to perform an equal angular magnification process and an angle adjustment process in the feature space as the selective expansion processing, an angle in a region R1x including a first reference line passing through the first color range being maintained unchanged based on an angle change rate W1x in the equal angular magnification process, an angle in a region R1y located outside the region R1x being changed based on an angle change rate W1y greater than or less than the angle change rate W1x in the angle adjustment process.

5. The image processing device according to claim 1, wherein the expansion processor includes a radial-coordinate adjuster configured to perform an equal radial-coordinate magnification process and a radial-coordinate adjustment process in the feature space as the selective expansion processing, a radial coordinate in a region R2x including a second reference line passing through the first color range and intersecting the first reference line passing through the first color range being maintained unchanged based on a radial-coordinate change rate W2x in the equal radial-coordinate magnification process, a radial coordinate in a region R2y located outside the region R2x being changed based on a radial-coordinate change rate W2y greater than or less than the radial-coordinate change rate W2x in the radial-coordinate adjustment process.

6. The image processing device according to claim 1, wherein the first color information is a first signal ratio between the image signals of the two colors out of the first red signal, the first green signal and the first blue signal and a second signal ratio between the image signals of the two colors different from the first signal ratio, and the feature space is formed by the first signal ratio and the second signal ratio.

7. The image processing device according to claim 1, wherein the first color information is chrominance signals Cr and Cb, and the feature space is formed by the chrominance signals Cr and Cb.

8. The image processing device according to claim 1, wherein the first color information is components a* and b* of color information of CIE Lab space, and the feature space is formed by the color components a* and b*.

9. The image processing device according to claim 1, wherein the first color information is hue and saturation, and the feature space is formed by the hue and the saturation.

10. The image processing device according to claim 1, further comprising:
a brightness adjuster configured to adjust a pixel value of the second red signal, the second green signal and the second blue signal based on first brightness information obtained from the first red signal, the first green signal and the first blue signal and second brightness information obtained from the second red signal, the second green signal and the second blue signal.

11. An endoscope system comprising:
an image sensor configured to image an object in a body cavity;
an input processor configured to perform an input process of a first red signal, a first green signal and a first blue signal output from the image sensor obtained by capturing a reflection image of an object in a body cavity;
a color information obtaining processor configured to obtain first color information from the first red signal, the first green signal and the first blue signal, the first color information being included in one of color ranges in a feature space formed by the first color information, according to a condition of the object;
an expansion processor configured to obtain second color information by a selective expansion processing in which color ranges except a first color range are moved in the feature space to expand a distance between the first color range and the other color ranges in the feature space, the first color range corresponding to a normal part in the object, and the other color ranges corresponding to different abnormal parts in the object;
an RGB signal converter configured to convert the second color information to a second red signal, a second green signal and a second blue signal; and
a pseudo-color display processor configured to obtain a red display signal, a green display signal and a blue display signal for displaying a medical image, by applying a pseudo-color display process to the second red signal, the second green signal and the second blue signal.

12. The endoscope system according to claim 11, further comprising:
a light source configured to irradiate at least one of violet light and blue light in addition to green light and red light to the above object; and
a source controller configured to independently control a light quantity of at least the one of violet light and blue light, a light quantity of the green light and a light quantity of the red light,
wherein the source controller performs a specific light quantity control to make the light quantity of at least the one of violet light and blue light and the light quantity of the green light larger than the light quantity of the red light, and the image sensor images the object irradiated with the light from the light source under control of the specific light quantity control.

13. The endoscope system according to claim 11, wherein the image sensor has a blue pixel, a green pixel and a red pixel, and
wherein the endoscope system further comprises an image controller configured to control the blue pixel, the green pixel and the red pixel, the image controller performing a specific imaging control to make the sensitivities of the blue pixel and the green pixel higher than the sensitivity of the red pixel.

14. A method of processing medical image for operating an image processing device comprising the steps of:
an input processor performing an input process of a first red signal, a first green signal and a first blue signal obtained by capturing a reflection image of an object in a body cavity;
a color information obtaining processor obtaining first color information from the first red signal, the first green signal and the first blue signal, the first color information being included in one of color ranges in a feature space formed by the first color information, according to a condition of the object;
an expansion processor obtaining second color information by a selective expansion processing in which color ranges except a first color range are moved in the feature space to expand a distance between the first color range and the other color ranges in the feature space, the first color range corresponding to a normal part in the object, and the other color ranges corresponding to different abnormal parts in the object;
an RGB signal converter converting the second color information to a second red signal, a second green signal and a second blue signal; and
a pseudo-color display processor obtaining a red display signal, a green display signal and a blue display signal for displaying a medical image, by applying a pseudo-color display process to the second red signal, the second green signal and the second blue signal.

* * * * *